United States Patent [19]

Miyazaki et al.

[11] Patent Number: 5,171,132
[45] Date of Patent: Dec. 15, 1992

[54] TWO-VALVE THIN PLATE MICROPUMP

[75] Inventors: Hajime Miyazaki; Masaaki Handa; Taisuke Uehara; Tsukasa Muranaka; Shinichi Kamisuki; Yasuto Nose, all of Suwa, Japan

[73] Assignee: Seiko Epson Corporation, Tokyo, Japan

[21] Appl. No.: 633,575

[22] Filed: Dec. 21, 1990

[30] Foreign Application Priority Data

| Dec. 27, 1989 | [JP] | Japan | 1-340469 |
| Jan. 31, 1990 | [JP] | Japan | 2-19241 |
| Jan. 31, 1990 | [JP] | Japan | 2-19242 |
| Feb. 8, 1990 | [JP] | Japan | 2-27170 |

[51] Int. Cl.$^5$ .................................. F04B 17/00
[52] U.S. Cl. ............................ 417/413; 417/322
[58] Field of Search ............ 417/322, 410, 413, 479

[56] References Cited

U.S. PATENT DOCUMENTS

| 649,886 | 3/1987 | Igashira et al. | 123/498 |
| 4,520,375 | 5/1985 | Krall | 417/410 |
| 4,636,149 | 1/1987 | Brown | 417/413 |
| 4,842,493 | 6/1989 | Nilsson | 417/410 |
| 4,911,616 | 3/1990 | Laumann, Jr. | 417/413 |
| 4,938,742 | 7/1990 | Smits | 417/322 |
| 4,939,405 | 7/1990 | Okayama et al. | 417/410 |

FOREIGN PATENT DOCUMENTS

| 0418644 | 3/1991 | European Pat. Off. | 417/479 |
| 112678 | 4/1990 | Japan . | |

Primary Examiner—Richard A. Bertsch
Assistant Examiner—Alfred Basichas
Attorney, Agent, or Firm—W. Douglas Carothers, Jr.; Gregory D. Ogrod

[57] ABSTRACT

A micropump particularly suited for use in the fields of medicine and analysis includes a thin membrane plate sandwiched between a surface plate and a glass-made substrate. The intermediate membrane has an inlet valve and an outlet valve and the glass substrate has an inlet port and an outlet port, respectively connected to the corresponding valves. Between the valves formed in the thin membrane plate by means of etching, there is a diaphragm on which there is a piezoelectric element for detecting behavior of the diaphragm. Another micropump has an upper thin membrane plate member and a lower member. The upper member has the inlet valve and the lower member has the outlet valve. An intermediate glass substrate is inserted between the upper and the lower thin membrane plate member.

31 Claims, 18 Drawing Sheets

SUCTION                     DISCHARGE

| DISORDER \ DETECTED POSITION | DIAPHRAGM | OUTLET VALVE |
|---|---|---|
| (a) AIR IS IN PUMP |  |  |
| (b) CLOGG OF PUMP, TUBE |  | THE SAME AS LEFT |
| (c) LEAK IN PUMP | THE SAME AS a | THE SAME AS a |
| (d) CRACK IN DRIVE PIEZOELECTRIC ELEMENT  BROKEN LEAD |  |  |
| (e) BACK PRESSURE KEEP OUTLET VALVE OPEN  VALVE IS BEST OPEN |  |  |

WHOLE SURFACE THERMAL OXIDIZATION

REAR FACE PATTERNING

REAR FACE ETCHING

BOTH FACES PATTERNING

BOTH FACES ETCHING

THERMAL OXIDIZATION MEMBRANE

ADHERING MEMBRANE FORMED

WHOLE SURFACE THERMAL OXIDIZATION

THIN MEMBRANE PLATE FORMING COMPLETED

TWO-VALVE THIN PLATE MICROPUMP

BACKGROUND OF THE INVENTION

The present invention relates to micropumps, particularly to such devices for the precise control of fluid discharge in medical and analytical applications and to a method of applying silicon micromachining technology to the manufacture of such micropumps.

Referring to FIG. 33, micropumps of the prior art include a glass substrate or base plate 200, glass plate 205 and silicon membrane 201 bonded therebetween. Membrane 201 includes diaphragm 204 formed between valves 202, 203. The diaphragm is adapted to be driven through air layer 206 by exothermic resistor 207. Glass substrate 200 has inlet port 208 and outlet port 209 in communication with a respective valve 202, 203. When air in layer 206 is thermally expanded, diaphragm 204 is displaced downwardly thereby increasing pressure within pump chamber 210. Such pressure closes inlet valve 202 and simultaneously opens outlet valve 203 thereby discharging fluid in pump chamber 210 to outlet port 209. When air layer 206 contracts, diaphragm 204 is displaced upwardly, valves 202, 203 function in reverse so that inlet port 208 draws fluid into chamber 210 and outlet port 209 prevents fluid discharge. Such micropumps precisely control the flow and discharge of minute volumes of fluid and are particularly adapted to medical and analysis applications.

Prior art methods for the manufacture of micromechanical devices including micropumps employ semiconductor etching technology including aerotropic etching and similar machining methods for forming complicated three-dimensional silicon construction. Such methods for making various shapes of joined substrates include substrate joining technology, an anode joining method for connecting substrates of glass and silicon. Silicon-formed pressure sensors have been developed as micromechanical devices, however, no established and reliable method for the manufacture of high performance micropumps is presently available.

Conventional micropumps have several shortcomings. The first of these relates to discharge performance. Two-valve type micropumps, as illustrated in FIG. 33, are easier to manufacture than three-valve type micropumps. However, two-valve devices experience gradual lowering of fluid flow volume due to pressure-differential P between the inlet and outlet ports, thereby deteriorating micropump efficiency. The characteristics curves of FIG. 34 show that two-valve type micropump flow volume Q decreases linearly with increasing pressure differential P, as illustrated by line A. In the case of three-valve type micropumps, depicted by line B, flow volume Q is substantially independent of variations in pressure differential P. The third valve provided in the flow route between the inlet and outlet valves prevents back-flow due to pressure differential P and thereby sustains constant flow volume. In the case of two-valve micropumps, however, the pressure differential P is applied directly to the outlet valve so the outlet valve experiences substantial force in the closing direction. When the two-valve type micropump is employed to administer insulin, for example, back pressure of about 600 mm $H_2O$ prevents discharge. In medical applications, fluid discharge is generally required at a substantially constant rate until back pressure reaches about 400 mm$H_2O$.

The second problem relates to securing the micropump drive means. Conventional methods often result in incomplete and ineffective installation of micropump drive apparatus. Generally, piezoelectric elements have been employed as drive apparatus because of their preferable controllability. The piezoelectric element must be uniformly bonded to the micropump drive diaphragm. Bonding a very thin membrane to the diaphragm is problematic. Because the diaphragm is secured at its periphery and is apt to bend or flex during bonding. As a result, a poor bond is attained between the piezoelectric element and diaphragm. If the piezoelectric element is pressed excessively to the diaphragm, the diaphragm periphery is stretched and subject to damage. This pressing force is difficult to control resulting in a difficult bonding operation.

The third problem concerns maintaining constant discharge performance, particularly in medical applications involving, for example, the administration of insulin. Medication over-dosing is a dangerous problem. It is necessary to immediately detect injection malfunctions due, for example, to breakdown of the micropump drive apparatus, blockage in an output needle, blending air in the pump, or valve breakage. No such detection means is provided in conventional micropumps.

The method of manufacturing micropumps having a thin membrane single crystal silicon diaphragm and a valve membrane integrally formed of single crystal silicon, and glass substrates sandwiching the thin membrane diaphragm employ fabrication methods for constructing silicon pressure sensors. However, the valve membrane includes a narrow zone defining a valve portion, through which zone the glass substrates come into contact with each other creating a small gap, deteriorating the seal. It is necessary to apply pre-pressure to such construction, however there has been no suitable means of providing such pre-pressure. When the glass plate and the main thin membrane are adhered by anode joining, the valve portion adhers to the glass plate rendering the valve body useless.

SUMMARY OF THE INVENTION

The micropump according to the present invention includes a thin membrane adhered to the upper substrate face. The membrane has an inlet port and an outlet port, and inlet and outlet valves for opening and closing a respective port, a fluid flow route, a surface plate secured to an upper surface of the thin membrane and a diaphragm defining a pump chamber. A surface plate is secured to an upper surface of the thin membrane. The micropump also includes means for driving the diaphragm. The outlet valve includes a cup-shaped valve body covering the outlet port.

According to one embodiment of the present invention, back pressure raises the valve body at the outlet valve. Force in the direction of flow raises the partition wall defining the outlet valve by means of the pressurized fluid from the pump chamber. When these opposing forces are identical it is possible to discharge at a substantially constant flow rate within the practical range of micropump usage until back pressure overcomes the sealing force. Consequently, two-valve type micropumps of the present invention achieve substantially the same discharge performance as prior art three-valve type micropumps with reduced size and cost.

It is preferable to employ a compact and controllable piezoelectric element as the drive means for the micropump diaphragm. The piezoelectric element is secured to the diaphragm and oscillates to vibrate the diaphragm up and down so as to vary pressure in the pump chamber. Such a structure operates quickly without raising fluid temperature.

Input fluid is lead directly into the chamber having the inlet port valve, however, according to the present invention, the input fluid is preferably lead to the chamber on the inlet port valve side from another chamber formed above a partition wall of the outlet port valve. When a sudden outside force is applied to the liquid in the micropump reservoir, it is possible to transfer such pressure surge to the chamber above the partition wall of the outlet valve. Closure of the outlet valve prevents fluid discharge in response to such surge.

The pump chamber is in communication with a chamber provided above a partition wall of the inlet valve and to the chamber having the outlet valve. In this embodiment, pressure in the pump chamber is transferred directly to the other two chambers, so as to actuate the periodic opening and closing operations of the inlet and outlet valves. To detect and control operation of the outlet valve, a top surface of the partition wall of the outlet valve is exposed to atmosphere and sensor means for detecting movement of the partition wall, such as a piezoelectric element or a strain gauge, is secured to the partition wall. It is possible to construct an inlet valve having a cup-shaped valve body, similar to that of the outlet valve, covering the inlet port. A piezoelectric element so installed on the outlet valve partition wall controls operation of the outlet valve, resulting in a more stable outlet valve seal.

When an intermediate substrate made of the same material as the thin membrane plate is sandwiched between the first substrate and the thin membrane plate. The intermediate substrate is etched to position and extends the inlet and outlet ports transversely of the intermediate substrate for easy connection to the tubes.

In applications where thickness of the micropump may vary relative to its horizontal area, it is possible to include a thin membrane plate of two-layer construction with an intermediate substrate inserted between them. In such structure, the upper thin membrane plate has an inlet valve and a pump chamber, and the lower thin membrane plate has an outlet valve. The intermediate substrate includes a first flow route connecting the inlet port to the chamber of the inlet valve and a second flow route connecting the pump chamber to the outlet valve chamber. Operation of the layered micropump is the same as that of the one-layer micropump.

When a support in contact with the substrate is provided to the diaphragm center, the support functions as a stopper and, along with the secured diaphragm periphery, resists forces applied to the drive piezoelectric element while adhering the piezoelectric element. As a result, it is possible to keep the surface of the diaphragm flat while connecting the piezoelectric element so as to obtain a uniform and stable bond between the drive piezoelectric element and the diaphragm. Though the support is ordinarily rod shaped, it is possible to alter the shape to that of a cylindrical or convex projection, for example, installed diametrically on the diaphragm thereby providing greater diaphragm stability. It is also possible to bring the diaphragm into direct contact with the substrate for support.

Where the diaphragm has such support and comes into contact with the substrate, operating the diaphragm as a stopper, the amplitude of the diaphragm is always constant, achieving a stable volume discharge. In particular, the diaphragm oscillates in half cycles due to the stopper, thereby decreasing discharge volume. Total discharge volume of the micropump may be increased according to the present invention by increasing the number of discharge cycles, raising the drive voltage or both.

When the support and diaphragm are separated, the support is a cylindrical projection integrally formed on the thin membrane plate. Front ends of the projection contact the central portion of the diaphragm. The projection functions as a stopper, as mentioned above, and as a flow rate control valve by forming a central opening in the projection for fluid flow or discharge at a fixed rate to the output side.

When means for detecting motion is mounted to the diaphragm, it is possible to correctly sense diaphragm oscillation waveshapes and detect abnormalities. The same principle can be applied to the outlet valve member. It is convenient and economical to use a piezoelectric element as the detection means. The piezoelectric element sensor may be fixed to a vibrating surface plate connected to the partition wall of the outlet valve through the vibration transferring projection, or directly onto the partition wall.

These diaphragm and valve sensors are employed individually or in combination in the micropump of the present invention. The sensors include a detection circuit for comparing the detected waveshape to a standard voltage at regular intervals during the period of rising waveshape and determining whether the flow is normal or abnormal by the order of highs and lows. According to the method of evaluating the result detected, it is possible to identify the detected waveshape following amplification through its rising curve. In particular, the waveshapes are compared to a standard voltage at regular intervals by seeing the order of highs (H) and lows (L). For example, when the order of waves of L-H-H is obtained, the flow is evaluated to be normal, and when the wave height order differs from the normal order, it is evaluated to be abnormal. It is preferable to apply pre-pressure to the sealing portion of the inlet and outlet valves to improve the resulting seal.

The manufacturing method of the present invention includes a thin membrane plate forming step for fabricating the main member of the micropump main body from a (100) face-direction silicon wafer having a diaphragm, routes, and valves of predetermined sizes integrally formed in the wafer, and another forming step comprising the application of pre-pressure to the valves by means of mask sputtering on the valve portions in contact with a substrate surface.

The thin membrane plate of the micropump is formed on the silicon wafer by means of wet-type anisotropy etching to form deep machinable grooves having flat bottoms and a constant taper angle for construction of valve and pump portions having suitable structure.

Because adhering membranes are deposited on the valve portions in contact with the glass substrate of the thin membrane plate before assembly by means of a mask sputtering step, the valve portions do not come into contact with the glass substrate during anode joining of the glass substrate and thin membrane plate. Due to the adhering membranes, pre-pressure is provided to the valve portion as described above to improve the seal between the glass substrate and the valve portion.

Accordingly, it is one object of the present invention to improve micropump discharge performance and to provide a micropump having a flow rate characteristic which is substantially constant within a predetermined range of pump usage.

It is another object of the present invention to provide a micropump having means to sense and control valve operation and having stable and secure valve seals.

It is still another object to provide a micropump having means to detect the operating condition of the micropump to attain correct micropump operation.

It is still another object to provide a manufacturing method for constructing such micropumps.

Other objects and attainments together with a fuller understanding of the invention will become apparent and appreciated by referring to the following description and claims taken in conjunction with the accompanying drawings.

DESCRIPTION OF THE INVENTION

Figure 1:
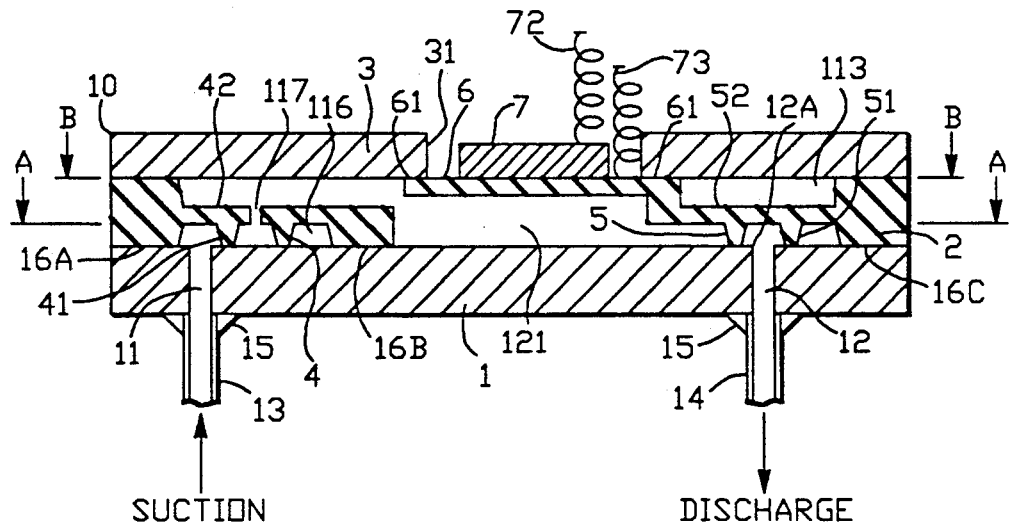
FIG. 1 is a section of one embodiment of the micropump according to the present invention.
Figure 2:
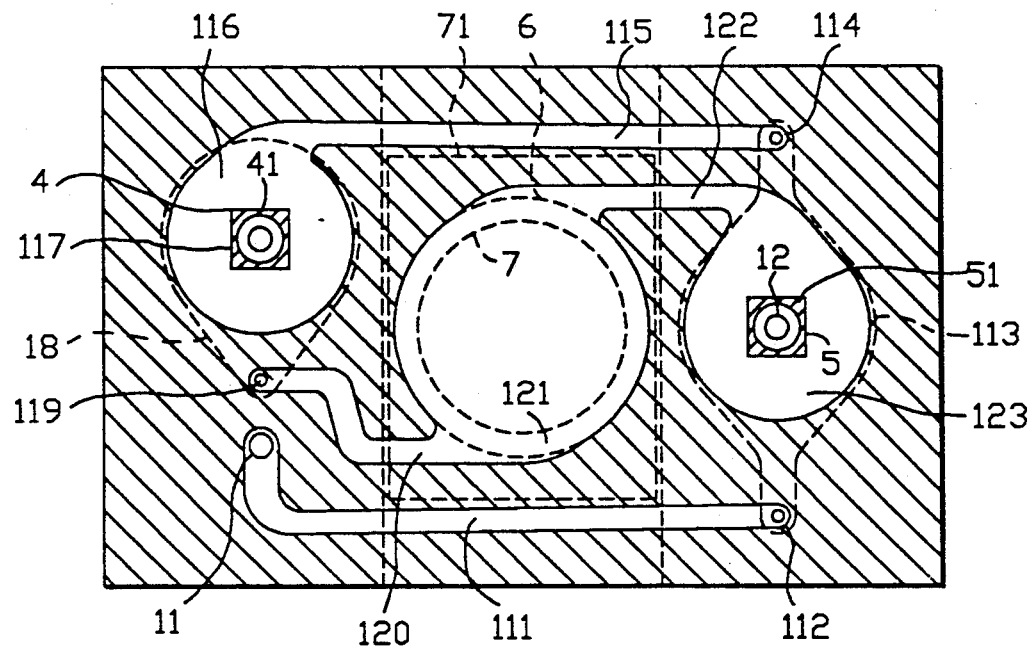
FIG. 2 is a cross-sectional view taken along line A—A of FIG. 1.
Figure 3:
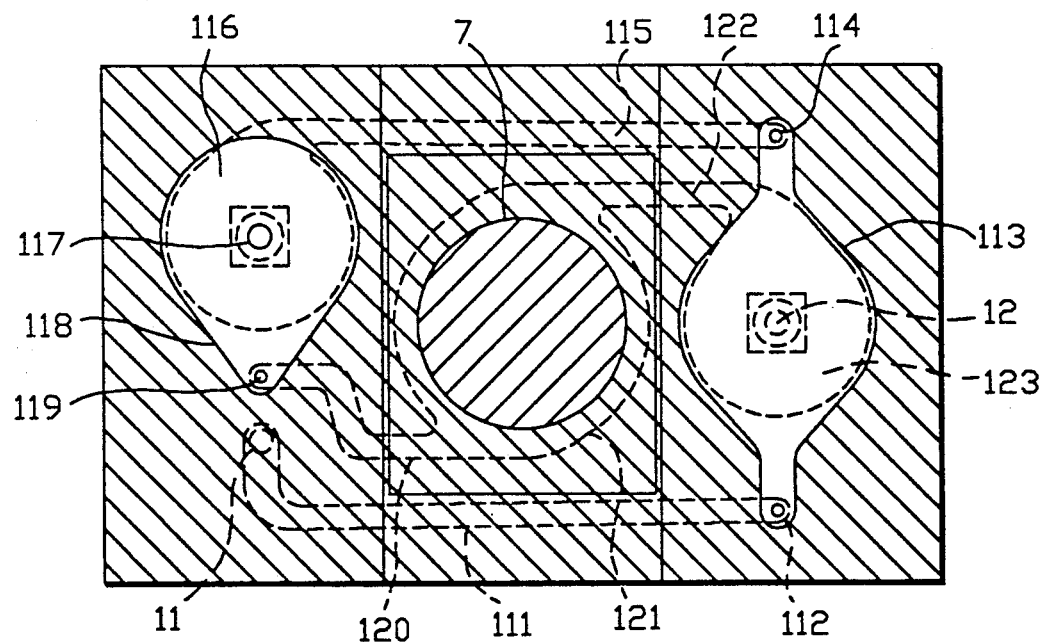
FIG. 3 is a cross-section view taken along line B—B of FIG. 1.

Referring to FIGS. 1-3, micropump 10 consists of substrate 1, surface plate 3 and thin membrane plate 2 sandwiched therebetween.

Substrate 1 is fabricated of glass plate having a thickness of about 1 mm. The substrate defines an inlet port 11 and an outlet port 12. Tubes 13 and 14 are secured water-tight to ports 11 and 12, respectively, by bonds 15. The base end of tube 13 is connected, for example, to a chemical reservoir (not shown) and a front end of tube 14 is joined for example to an injection needle (not shown).

Thin membrane plate 2 is a silicon substrate having a thickness of about 0.3 mm. Plate 2 includes inlet valve 4, outlet valve 5, diaphragm 6 positioned between valves 4, 5, and a flow route formed by an etching process. Thin membrane plate 2 is connected to the upper surface of substrate 1 by an anode joining method at joining positions 16a, 16b, 16c.

As shown in FIGS. 2 and 3, inlet port 11, formed in thin membrane plate 2, communicates with input passage 111. Passage 111 is in communication by means of passage hole 112 with chamber 113 formed above outlet valve 5. Passage hole 114 provides communication of fluid in chamber 113 with connecting passage 115 leading to chamber 116 of inlet valve 4. Inlet valve 4 includes square valve body 41 having central hole 117 leading to chamber 118 above valve body 41. Further, chamber 118 is in communication with pump chamber 121 below diaphragm 6 through hole 119 and connecting route 120. Thus, pressurized fluid flows to chamber 123 of outlet valve 5 through output route 122. Outlet valve 5 includes square cup-shaped valve body 51 covering discharge outlet 12a of outlet port 12.

Figure 19:
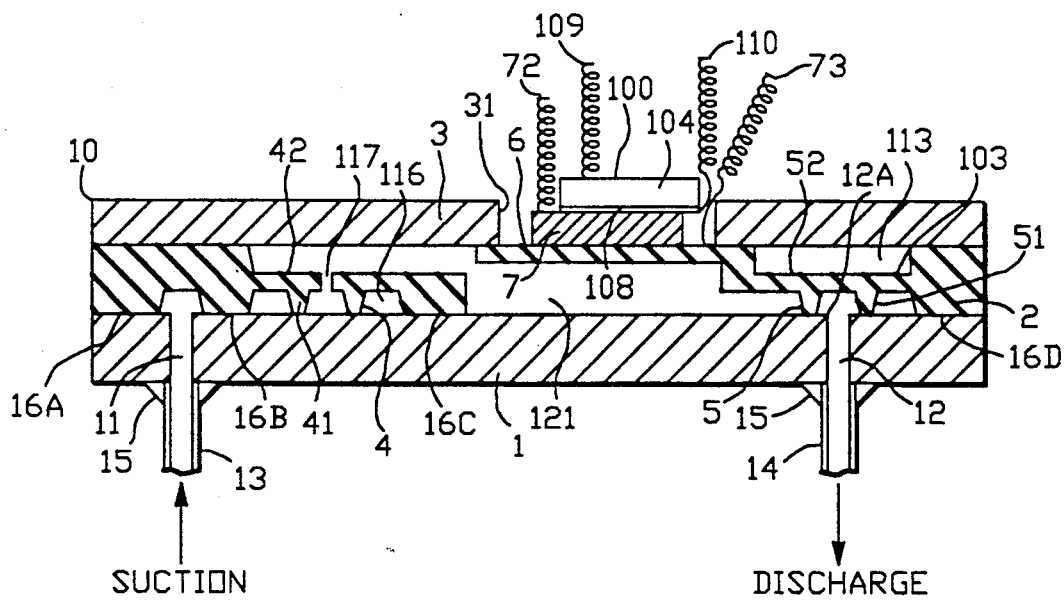
FIG. 19 is a section showing an embodiment of a detecting device applied to a diaphragm.

A piezo-disc having piezoelectric element 7 functions as drive means for diaphragm 6. Element 7 is secured to the upper surface of diaphragm 6 through thin membrane electrode plate 71. As seen in FIG. 19, leads 72, 73 apply voltage to piezoelectric element 7.

Figure 4:
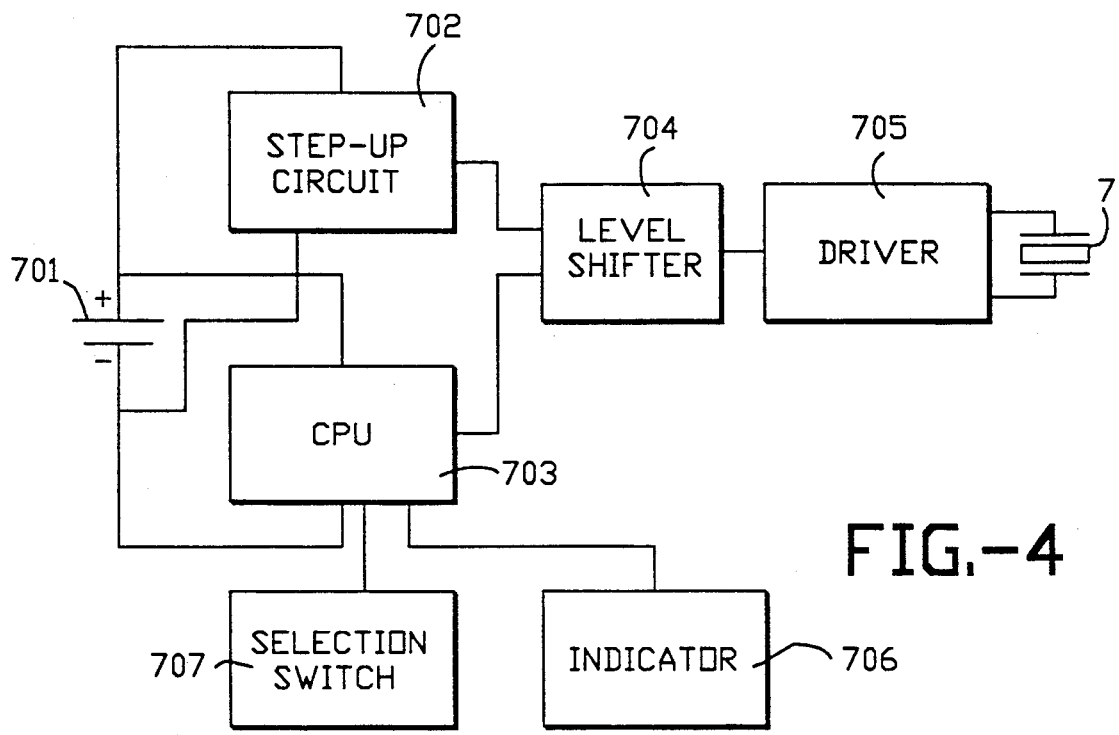
FIG. 4 is a block diagram illustrating a drive circuit for the drive piezoelectric element of the embodiment of FIG. 1.

Surface plate 3 of a glass substrate similar to substrate 1 is adhered by an anode joining method to the upper surface of thin membrane plate 2. Plate 3 defines pumping flow system insertion port 31 of piezoelectric element 7. Peripheral portion 61 of diaphragm 6 is adhered to the circumference of insertion port 31 having a thickness of about 0.5 mm. FIG. 4 depicts a block diagram of one embodiment of a circuit for driving piezoelectric element 7. The drive circuit includes power source 701, such as a lithium cell, stepup circuit 702, CPU 703, level shifter 704 for changing a low voltage signal to a high voltage signal, driver 705, indicator 706 for displaying the fluid flow rate, and flow rate selection switch 707.

In operation, referring to FIGS. 4 and 5 the flow rate is first selected by switch 707. CPU 703 outputs a drive signal. The signal issued from CPU 703 generally operates at a voltage of 3–5 V and piezoelectric element 7 operates at a high voltage such as 50 V. Stepup circuit 702 rises the voltage of 3 V to 50 V and level shifter 704 changes the signal from CPU 703 to another signal of 50 V.

Figure 5A:
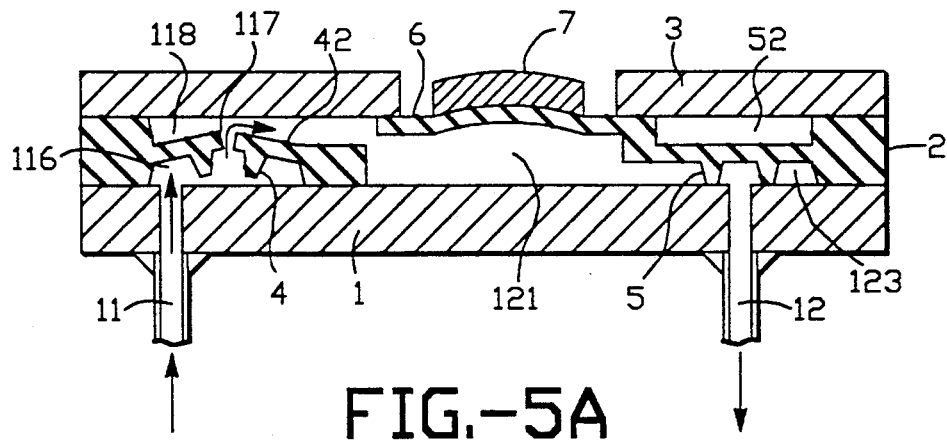
FIGS. 5(a), (b) are operation views of the embodiment of FIG. 1.

Alternating voltage of 50 V is periodically applied to piezoelectric element 7 providing oscillation in a range of one to several Hz. When diaphragm 6 deflects upward as shown in FIG. 5(a) due to piezoelectric effect, pressure in pump chamber 121 is reduced so that partition wall 52 of chamber 123 deflects downward to close outlet valve 5. As valve 5 closes, partition wall 42 of partition chamber 118 deflects upward so as to open inlet valve 4 resulting in fluid suction of predetermined volume from chamber 116 through hole 117.

Figure 5B:
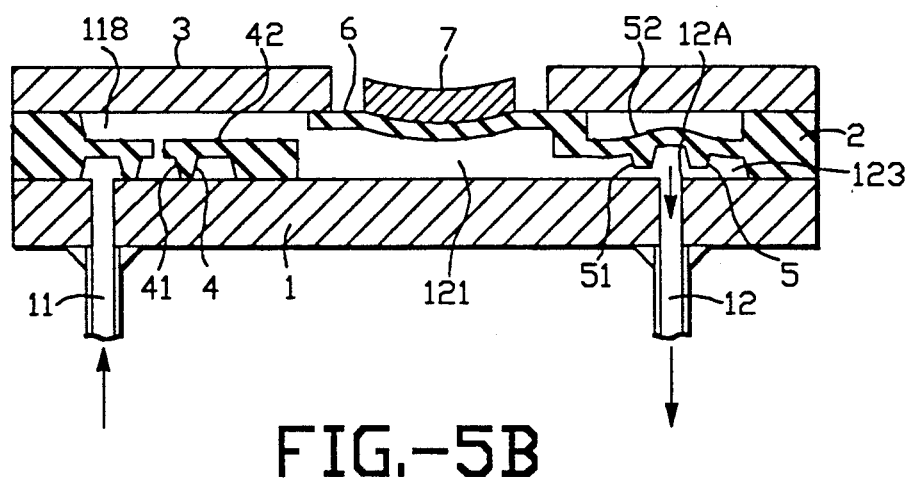

When diaphragm 6 is bent downward by piezoelectric element 7, as shown in FIG. 5(b), pressure in pump chamber 121 increases and is simultaneously transferred to chambers 118, 123 through routes 120, 122. The higher inner pressure of chamber 118 pushes partition wall 42 downward forcing valve body 41 against substrate 1, thereby closing inlet valve 4. The rising pressure in chamber 123 simultaneously pushes up partition wall 52 separating valve body 51 from substrate 1 thereby opening outlet valve 5 and discharging a predetermined volume of fluid through outlet port 12. The oscillation of diaphragm 6 by piezoelectric element 7 functions to continuously draw and discharge fluid. When oscillation frequency increases, a smoother fluid pumping operation having decreased pulsing is achieved.

In conventional two-valve type micropumps, back pressure operates to close the outlet valve so that larger back pressure requires more force to open the outlet valve. When the piezoelectric element is driven to raise the pump chamber pressure, amplitude of the piezoelectric element is restricted thereby decreasing the discharging flow volume in the conventional micropump with an increase in discharge pressure. Because outlet valve 5 of the present invention includes cup-shaped valve body 51 covering discharge outlet 12a of outlet port 12, the direction of operation of raising partition 52 (opening force of outlet valve 5) due to back pressure from outlet port 12 is the same as the direction of operation of the pressure in pump chamber 121 pushing partition 52, thereby diminishing back pressure restraint on the amplitude of the piezoelectric element. The micropump according to the present invention discharges at an almost-constant flow rate within a range of predetermined pump usage until back pressure overcomes the resilient force of outlet valve 5 and pressing force effective to partition wall 52 due to outside force.

Figure 34:
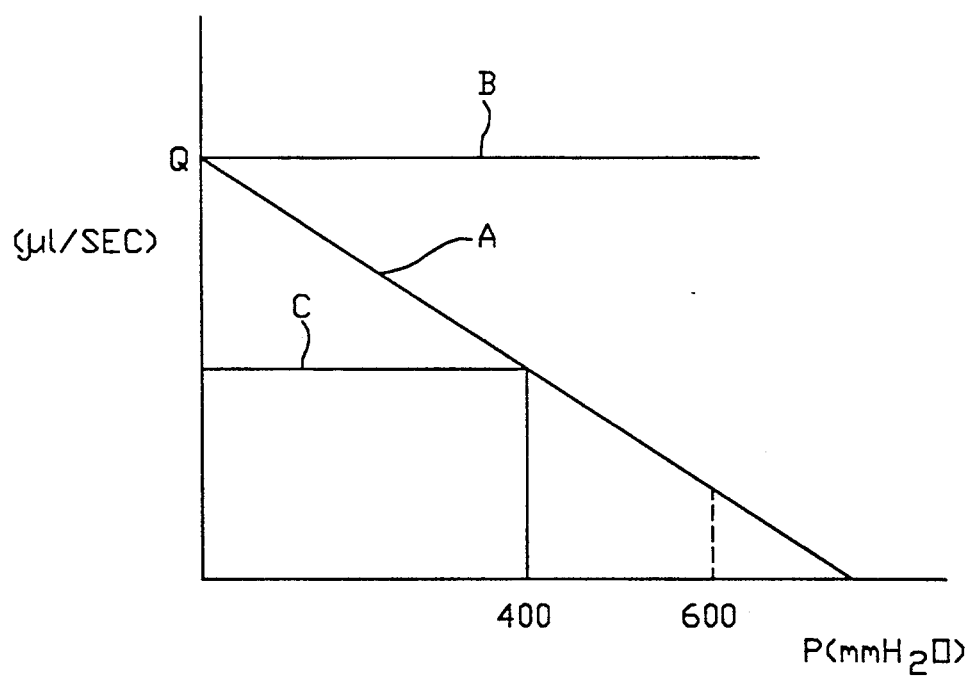
FIG. 34 is a diagram depicting performance characteristics of prior art pumps and the pump according to the present invention.

Pumping performance of the micropump of the present invention is shown in FIG. 34. The pumping performance of prior art micropumps is depicted by line C. As apparent from FIG. 34, the two-valve type micropump of the present invention enjoys the performance corresponding to prior art three-valve type devices with reduced manufacturing cost.

Figure 6:
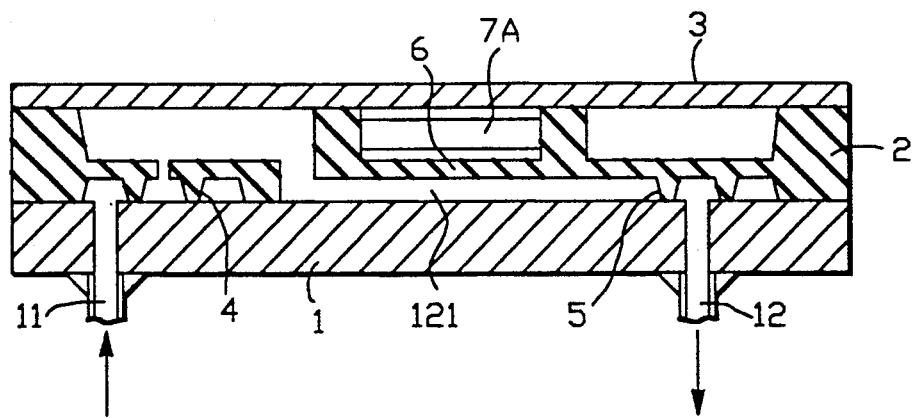
FIG. 6 is a construction view of the embodiment of FIG. 1 employing a dielectric as a drive means.

FIG. 6 illustrates a micropump embodiment employing a dielectric 7A as the drive means for diaphragm 6. The diaphragm is oscillated by static electricity force of dielectric 7A.

Figure 7:
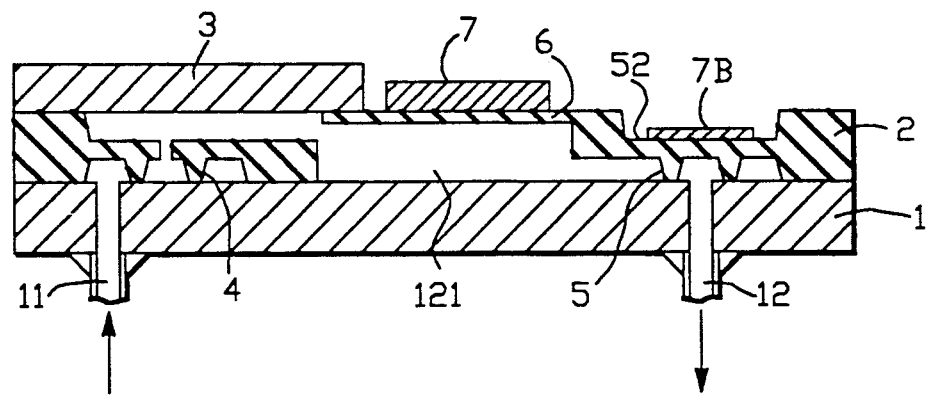
FIGS. 7 and 8 are sectional views depicting alternative embodiments of the present invention.

FIG. 7 depicts an alternative micropump embodiment without surface plate 3 placed above chamber 113. Accordingly, the upper surface of partition wall 52 of outlet valve 5 is exposed to atmosphere. Because input fluid is not led to chamber 113 above outlet valve 5 as in FIG. 1, it is not necessary to provide relief means for sudden input fluid pressure changes due, for example, to a sudden outside force applied to a resilient reservoir. Strain sensor 7B on partition wall 52 detects the sealing condition of outlet valve 5 and replaces relieve or other protective means for such sudden outside forces.

The seal of outlet valve 5 is held by elastic displacement of partition wall 52, so it is possible to control pumping operation by displacement detection. Knowing the relationship between the opening of outlet valve 5 and the micropump power, it is possible to control the fluid flow rate. In the embodiment depicted in FIG. 7B, piezoelectric elements can be substituted for the strain sensor.

Figure 8:
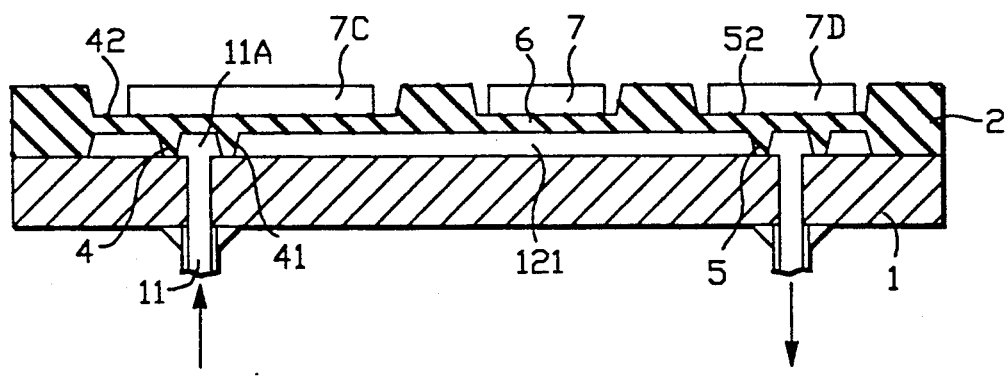

As illustrated in FIG. 8, surface plate 3 is omitted and piezoelectric elements 7C and 7D are secured to partition walls 42, 52 to control valve operation. Piezoelectric element 7D is provided at the side of outlet valve 5 to improve the seal of outlet valve 5. By synchronizing valve operation with operation of drive piezoelectric element 7 of diaphragm 6, it is possible to improve stability and accuracy of the pumping function. Valve body 41 is preferably cup-shaped to cover outlet 11a of inlet port 11 to attain a stabilized seal and thin construction.

Figure 9:
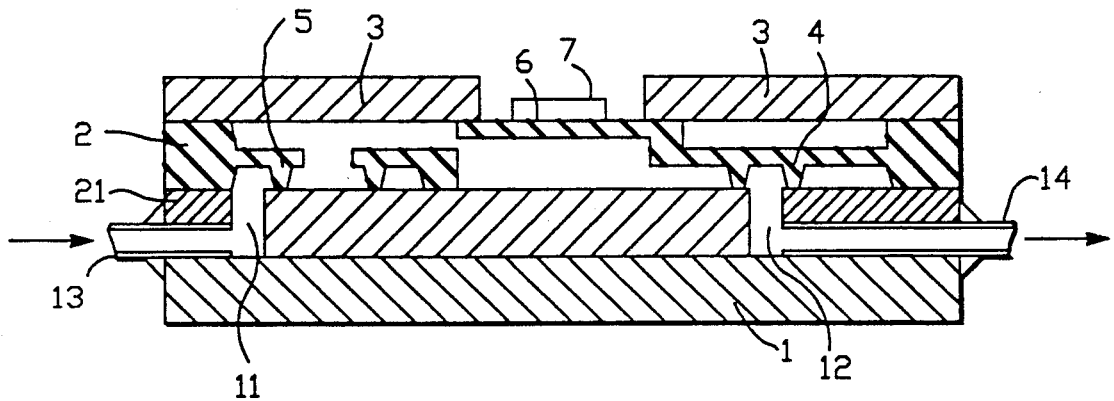
FIG. 9 is a construction view of an alternative embodiment of the present invention having a transversal inlet port and a transversal outlet port.

According to the embodiment of FIG. 9, an additional intermediate silicon substrate 21 placed between substrate 1 and membrane plate 2. Inlet port 11 and outlet port 12 are installed traversely in intermediate substrate 1. Inlet port 11 and outlet port 12 are economically fabricated in intermediate substrate 21 by means of an etching process. The micropump includes transversely extending tubes 13, 14 so extended tube portions do not occupy smaller spaces about the surrounding construction.

Figure 10:
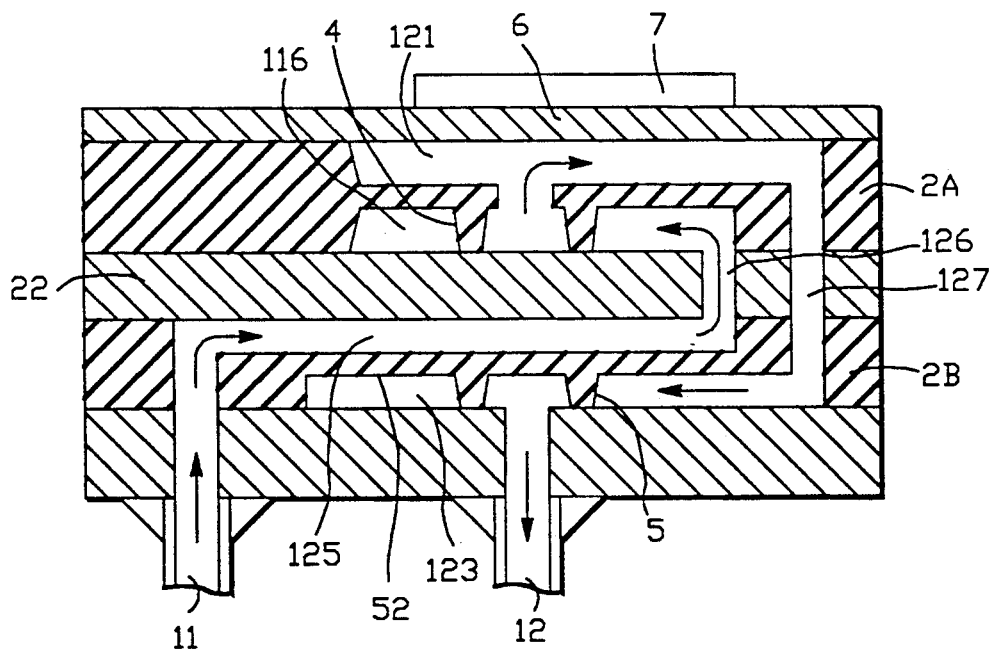
FIG. 10 is a constructional view of an alternative embodiment having two thin membranes layered through an intermediate.

FIG. 10 illustrates a micropump embodiment having an upper layer including inlet valve 4, and a lower layer including outlet valve 5. An intermediate glass substrate 22 is sandwiched between upper and lower thin membrane plates 2a, 2b. Plate 2a includes inlet valve 4 and pump chamber 121. Plate 2b includes outlet valve 5. Diaphragm 6 is secured to the upper surface of upper thin membrane plate 2a. Piezoelectric element 7 is fixed to diaphragm 6.

The micropump of FIG. 10 defines an overall cubic structure in contrast to the plane structures of the previous embodiments. Referring to FIG. 10, fluid inputted from inlet port 11 of substrate 1 flows through fluid route 125 formed above partition wall 52 of outlet valve 5 and through hole 126 of intermediate substrate 22 into chamber 116 of inlet valve 4. Pressurized fluid in pump chamber 121 enters chamber 123 of outlet valve 5 through through hole 127 formed in intermediate substrate 22 and discharges through outlet valve 5 into outlet port 12. This embodiment is particularly useful in applications having allowance in construction height (width).

Figure 11:
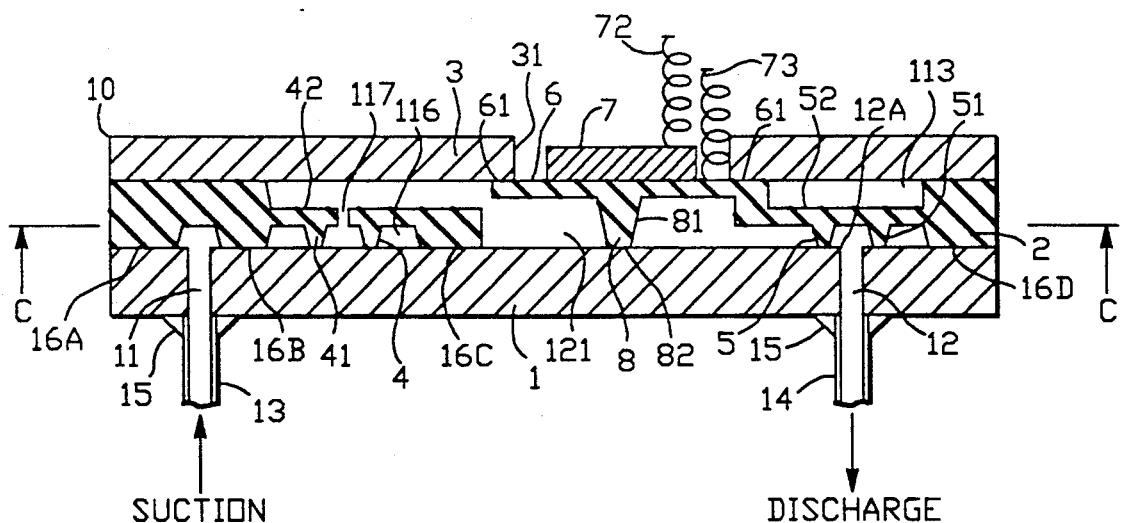
FIG. 11 is a section showing still another embodiment of the present invention.
Figure 12:
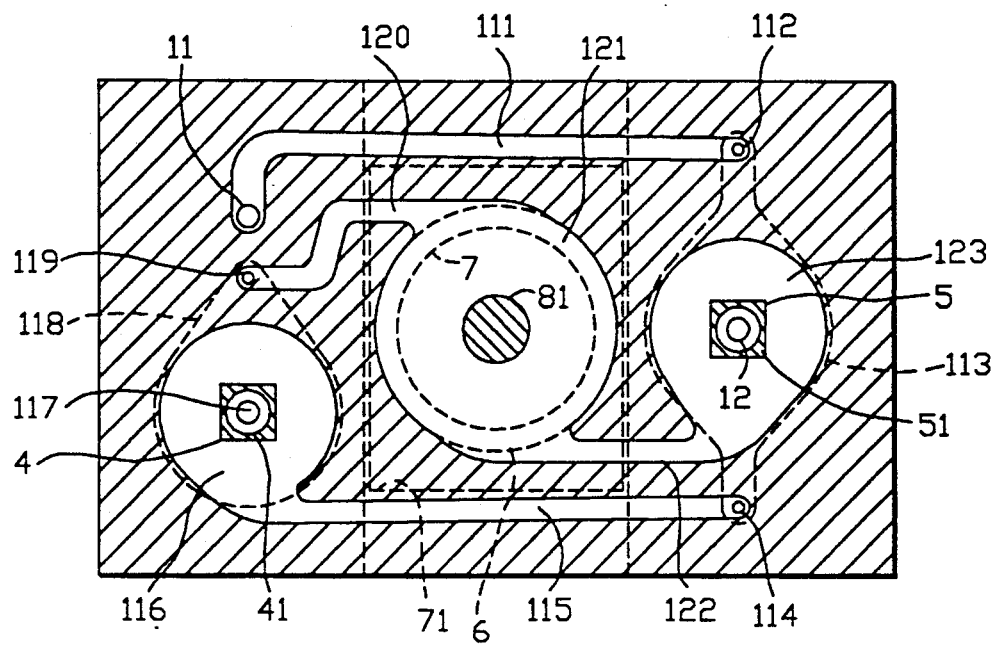
FIG. 12 is a section taken along line C—C of FIG. 11.

FIGS. 11 and 12 depict another embodiment of the invention having a support formed at the diaphragm center. This embodiment includes a support 8 comprising a rod-type projection 81 formed at the center of diaphragm 6 in contact with the surface of substrate 1. The shape of support 8 can be a circle, square or other suitable shape. Diaphragm 6 is supported by the contact of spherical portion 61 with surface plate 3, as well as by the central support of projection 81. Consequently, when drive piezoelectric element 7 is adhered to diaphragm 6, projection 81 functions as a pole or stopper and to reduce bending of diaphragm 6 while adhering piezoelectric element 7. Because of such support the flat surface of diaphragm 6 is sustained and piezoelectric element 7 securely and uniformly bonded. Also piezoelectric element 7 may be pressed with greater force during bonding without damage to the peripheral portion of diaphragm 6 thereby making the bonding step easier.

Figure 13A:
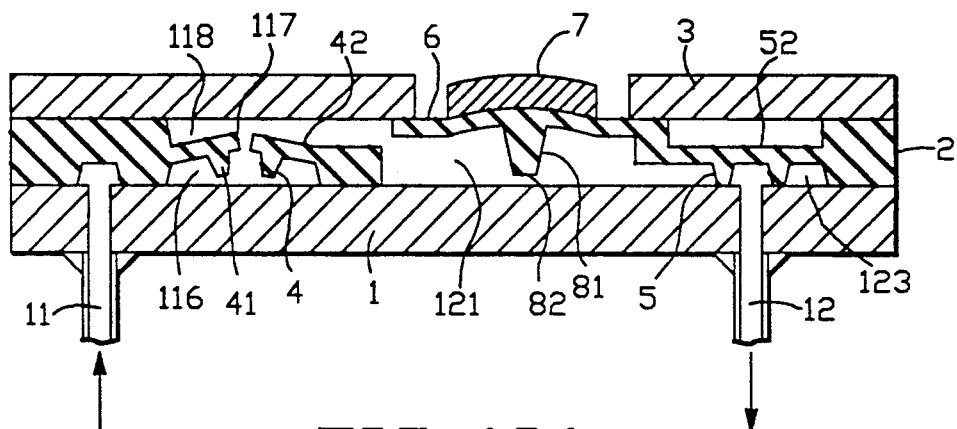
FIGS. 13(a)-(c), depict operative views of the embodiment of FIG. 11.
Figure 13B:
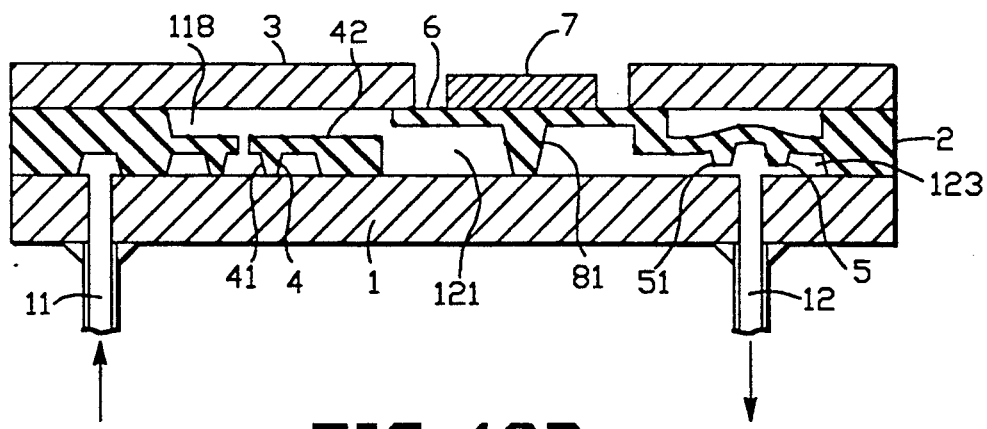
Figure 13C:
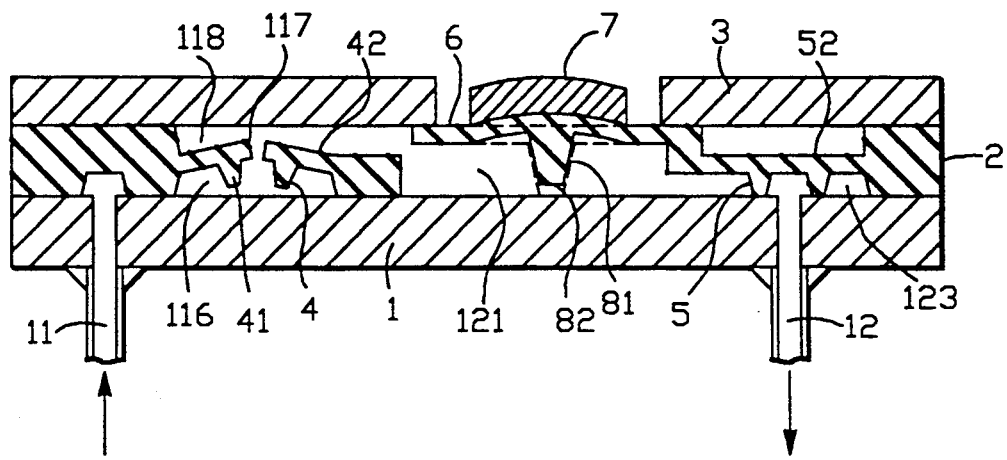
Figure 14:
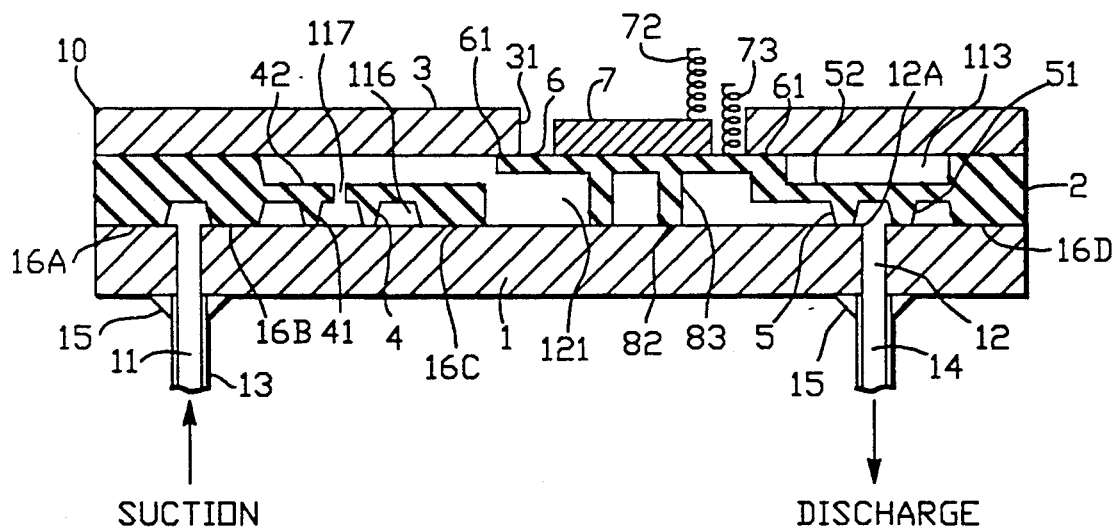
FIG. 14 is a section of an alternative embodiment of FIGS. 13(a)-(c) having a cylindrical projecting support.

The pumping and valving operation of the exemplary embodiment of FIG. 11 is substantially the same as that of the micropump depicted in FIGS. 4 and 5. However, because the amplitude of diaphragm 6 is made constant by means of the stopper function of projection 81, as seen in FIGS. 13(a)14 (c), a stable and constant flow is obtained. Although diaphragm 6 oscillates at half amplitude due to the stopper function thereby reducing discharge volume per oscillation, it is possible to achieve required discharge volumes by raising the number of discharging cycles or the driving electric voltage.

As depicted in FIG. 14, support 8 is in the form of a cylindrical projection 83 formed coaxially with diaphragm 6 to provide more stability to diaphragm 6. It is possible to combine the construction depicted in FIG. 14 with the embodiment of FIG. 11.

Figure 15:
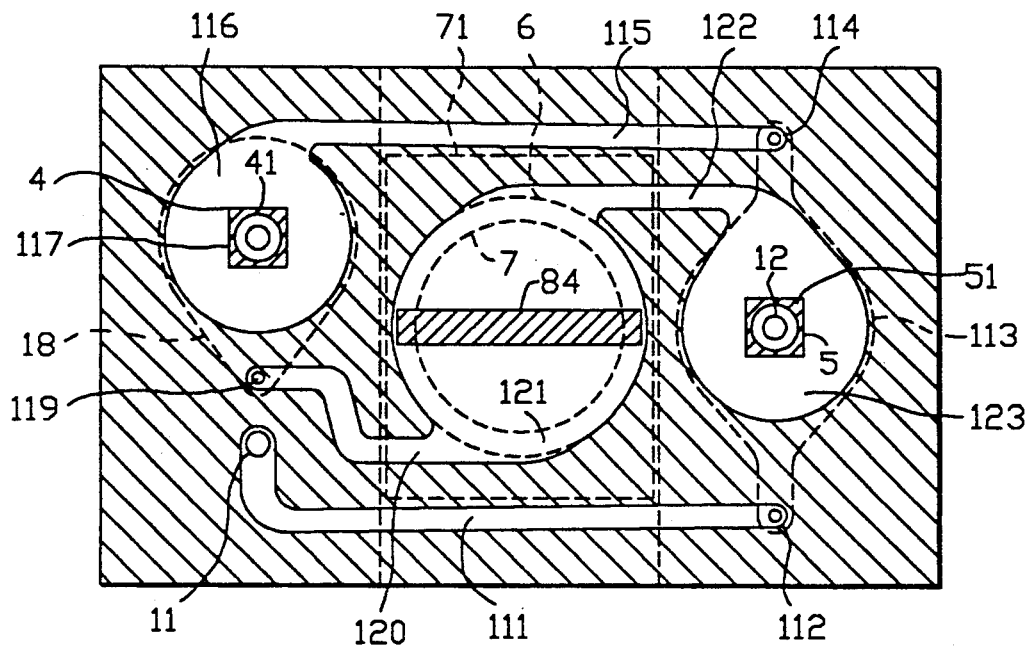
FIG. 15 is a section of an alternative embodiment of the present invention having a concave projecting support.

A plurality of rod-like projections 81, as shown in FIG. 11, may be arranged along the diameter of diaphragm 6. According to the embodiment of FIG. 15, convex projection 84 prevents outlet flow when a pressure surge is transmitted from inlet 11 and back-flow from the outlet valve.

Figure 16:
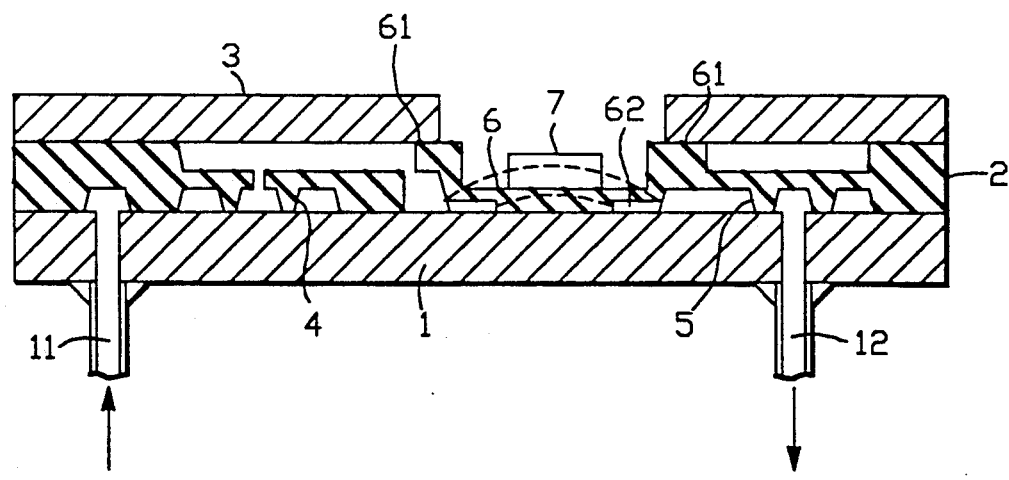
FIG. 16 is a section of an alternative embodiment of the present invention which employs the diaphragm as a support.

Projections 81, 83 and 84 are individually formed at the center of diaphragm 6 so as to come into contact with substrate 1 through the projection ends. Referring to FIG. 16, it is possible to eliminate these projections and provide for contact between a part of diaphragm 6 with substrate 1. The entire surface of diaphragm 6 comes into contact with substrate 1, so that adhering of piezoelectric element 7 thereto can be done more easily. In this case, the entire construction of diaphragm 6 oscillates in the upper space as shown by the broken lines depicted in FIG. 16 to carry out a pumping function. Grooves 62 are formed at the sides of connecting route 120 and output route 122 of diaphragm 6 in order to provide fluid flow through the grooves and gaps formed when diaphragm 6 is upwardly displaced.

Figure 17:
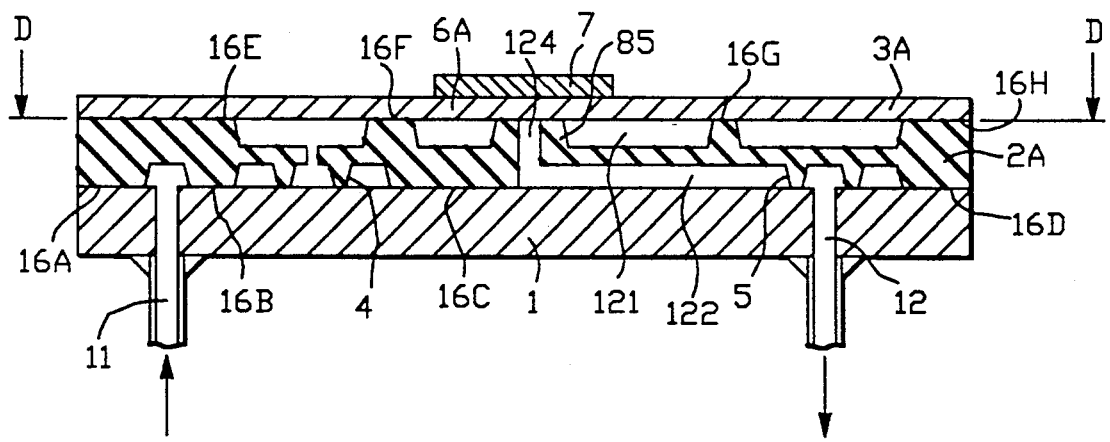
FIG. 17 is a section of an alternative embodiment of the present invention provided with a support portion having a valve function.
Figure 18:
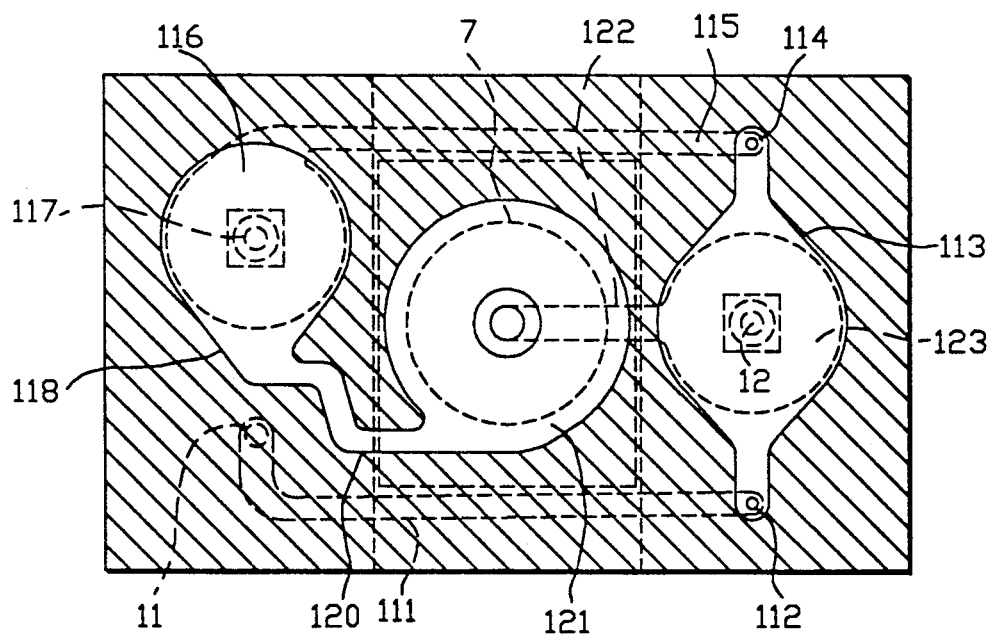
FIG. 18 is a section taken along line D—D of FIG. 17.

In the embodiment of FIG. 17, diaphragm 6A is integrally formed with a silicon or glass fabricated thin membrane surface plate 3A. Cylindrical projection 85, supporting the central portion of diaphragm 6A, is formed on thin membrane plate 2A to lead central hole 124 of projection 85 to output route 122 and to bond part of the bottom of projection 85, except for output route 122, to substrate 1. As seen in FIG. 11, portions 16a, 16b, 16c, 16d of thin membrane plate 2A are bonded to substrate 1, and the other bonding portions 16e, 16f, 16g, 16h of membrane plate 2A are bonded to surface plate 3A.

The front end of projection 85 comes into contact with the lower face of diaphragm 6A providing a stopper function and serving as a flow rate control valve for fluid led to the output side through central hole 124 so as to achieve a constant flow rate from oscillation of diaphragm 6A.

The micropump 10 of FIG. 19 includes detection apparatus 100 adapted to sense the behavior of diaphragm 102. Detection apparatus 100 consists of piezoelectric element 104 adhered to drive element 7 through insulation sheet 108. Detection piezoelectric element 104 has leads 109 and 110. Detection piezoelectric element 104 senses strain in drive piezoelectric element 7 as well as mechanical displacement of diaphragm 6. Such detection piezoelectric element 104 is of particularly low cost.

FIGS. 20-23 depict alternative embodiments employing the previously described valve mechanism, in particular to outlet valve portion 103 having detection apparatus 101 employed in conjunction with valve portion 103. Because outlet valve portion 103 provides open-and-shut movement at regular time intervals, it is possible to identify a disorder, as in the case of diaphragm 102, by detecting behavior of the valve portion.

Figure 20:
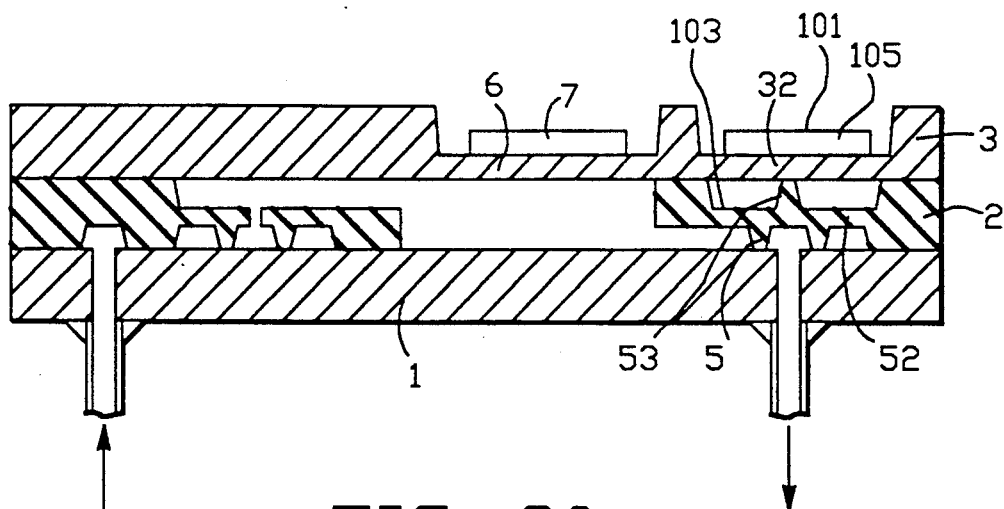
FIGS. 20-23 show various methods of securing the diaphragmapplied detecting device of FIG. 19.

As shown in FIG. 20, detection piezoelectric element 105 is fixed to oscillation portion 32 of surface plate 3 above outlet valve 5 made of a silicon substrate in order to connect oscillation portion 32 and partition wall 52 provided with outlet valve 5 through oscillation transferring projection 53. Behavior of outlet valve 5 appears in displacement of partition wall 52 and is transferred to oscillation portion 32 of the surface plate through projection 53. It is possible to indirectly detect behavior of outlet valve 5 by means of oscillation waveshape detection by piezoelectric element 105.

Figure 21:
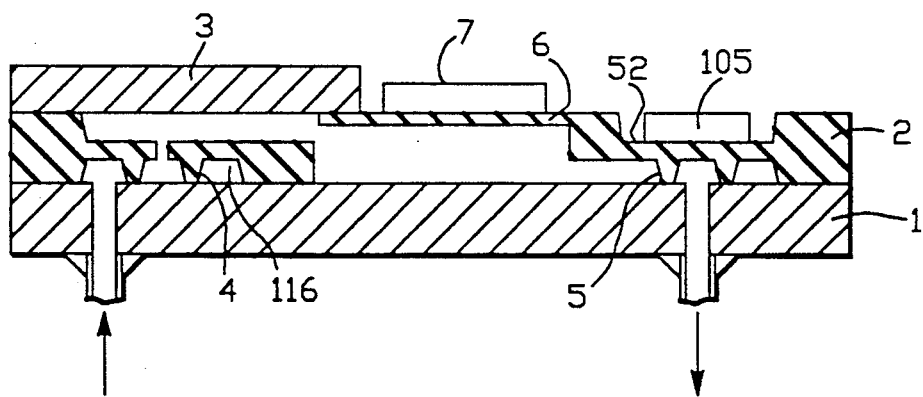
Figure 22:
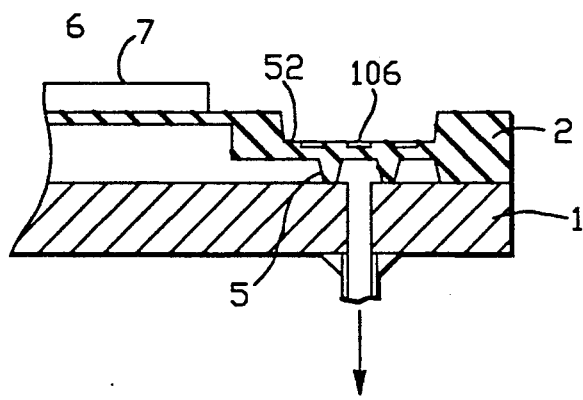
Figure 23:
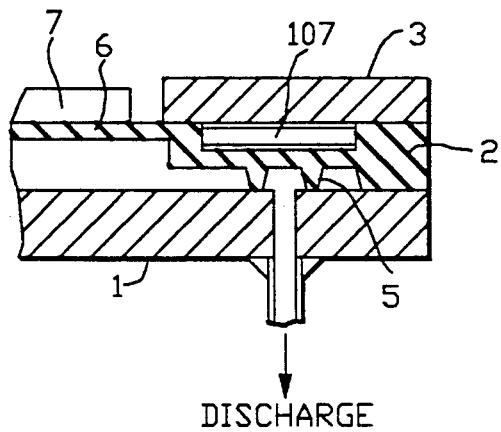

Similarly, the embodiment shown in FIG. 21 has detection piezoelectric element 105 secured directly to partition wall 52. Here, a part of surface plate 3 is moved to expose the upper surface of partition wall 52 and input fluid is led to chamber 116. FIGS. 22 and 23 show embodiments having diffused resistor 106 and dielectric 107, respectively, mounted on partition wall 52. Detection apparatuses 100, 101 can be used individually or in combination.

Figure 25A:
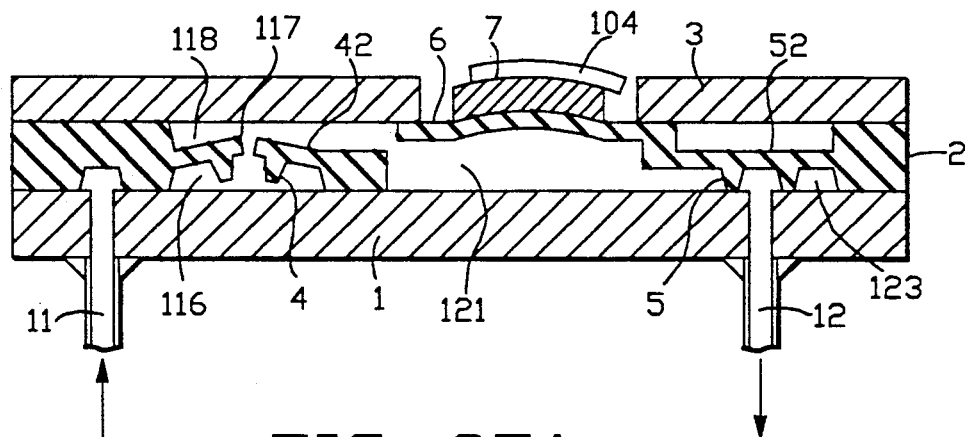
FIGS. 25(a), (b) are operational views of the embodiment of FIG. 19.
Figure 25B:
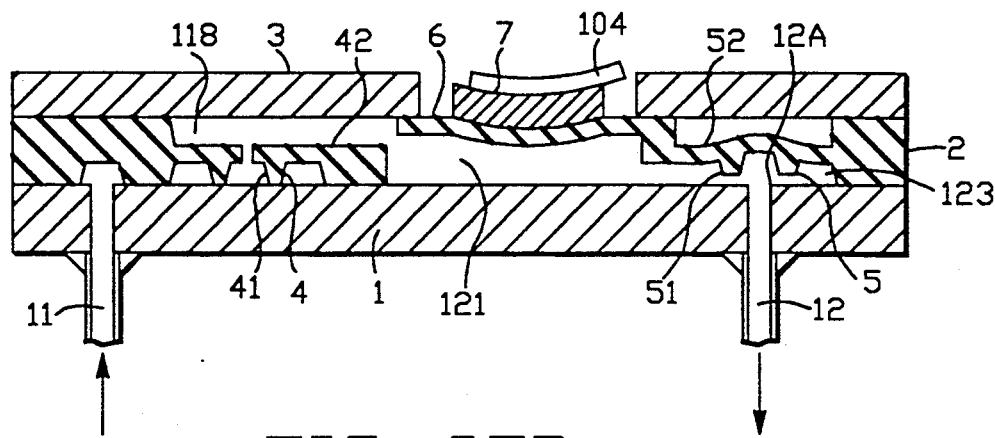
Figure 24:
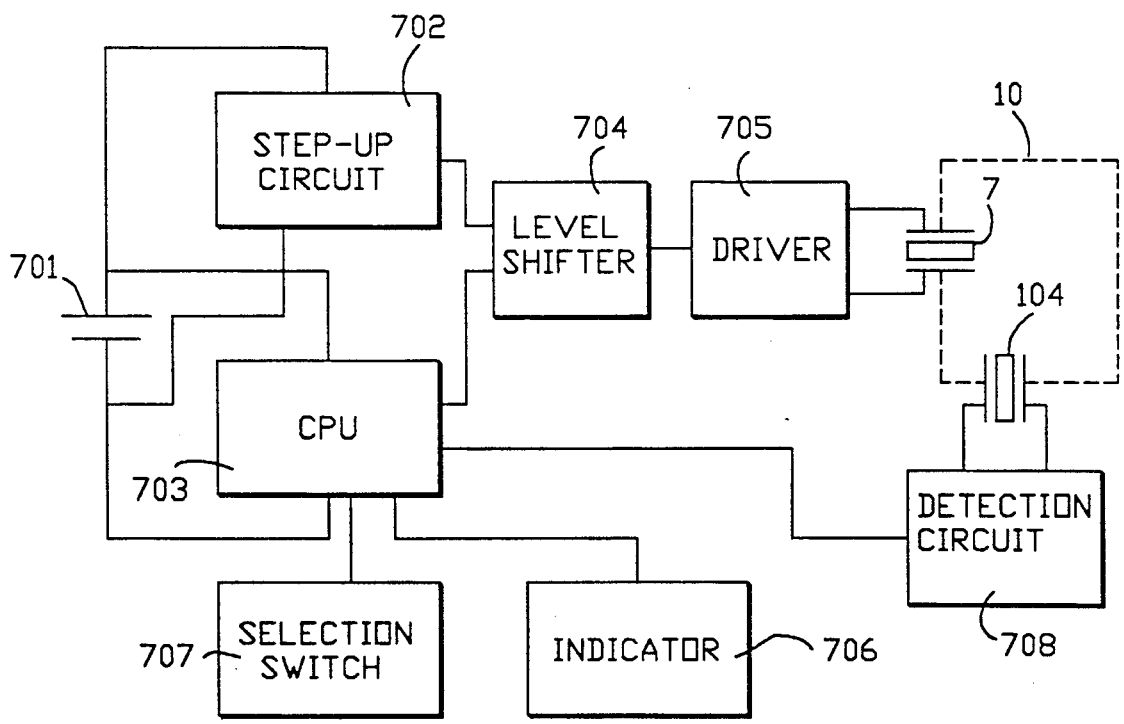
FIG. 24 is a block diagram of the circuit of the embodiment of FIG. 19.

FIG. 24 depicts a circuit to drive piezoelectric element 7, and additionally, for example, a detection circuit for diaphragm detection apparatus 100 employing a detection piezoelectric element 104. FIG. 25 depicts operation of the micropump of FIG. 19. The valve detection apparatus 101 also has a similar circuit structure. The pumping and valving operation of micropump 10 depicted in FIGS. 25(a)-(b) have been explained with reference to FIGS. 4 and 5. Operation of detection apparatus 100 and detection circuit 708 is initiated when a drive voltage is applied to piezoelectric element 7. The applied voltage and predetermined timing are instantly read by CPU 703 through detection piezoelectric element 104 and detection circuit 708. When a disorder is detected, CPU 703 may issue a drive stop signal and display device 706 display the disorder. Detection circuit 708 amplifies the voltage generated from detection piezoelectric element 104, and compares High (H) and Low (L) through operation of a comparator. The resulting signal is transmitted to CPU 703.

Figure 26:
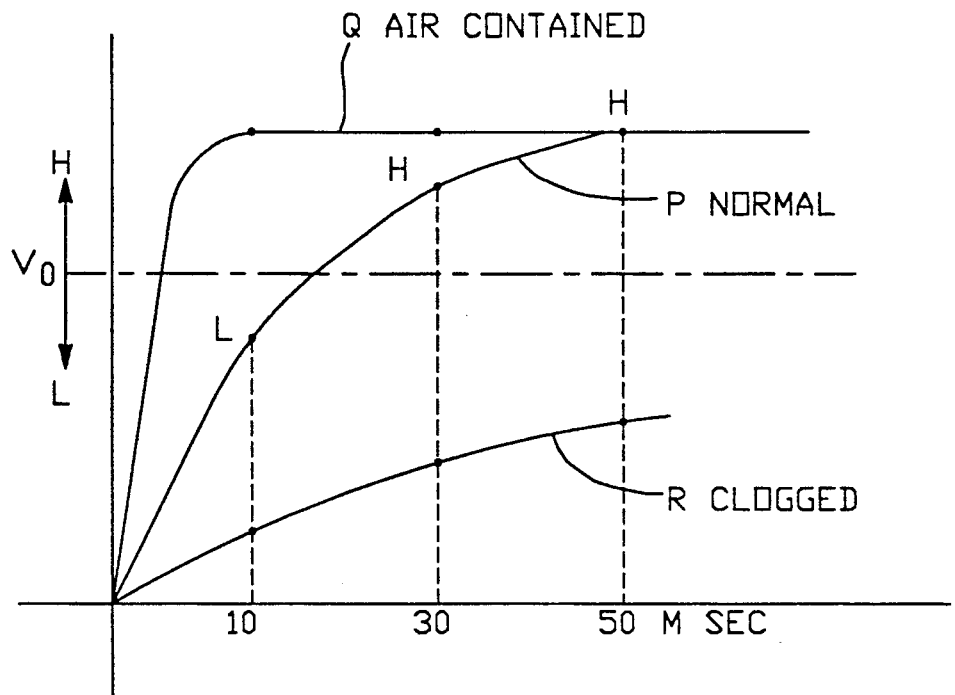
FIG. 26 is an explanation view of judging method of detected output waveforms.
Figure 27A:
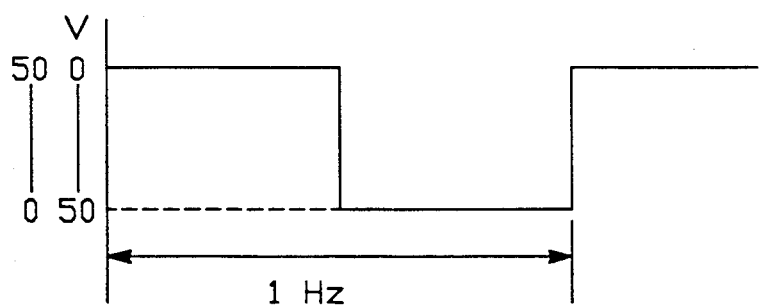
FIG. 27(a) depicts voltage pulse waveforms applied to the diaphragm drive piezoelectric element.
Figure 27B:
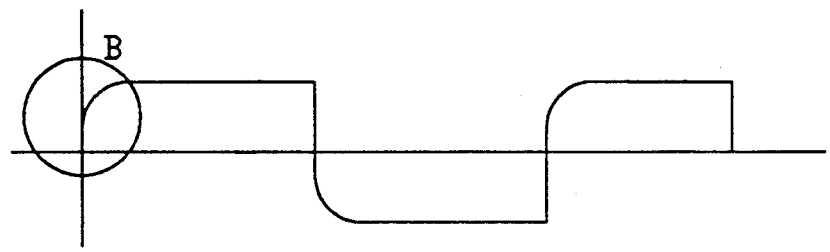
FIG. 27(b) depicts the output waveform of diaphragm detection piezoelectric element.

FIGS. 26 and 27(b) depict exemplary detection piezoelectric element 104 output waveshapes having enlarged rising portion B for the diaphragm when, as depicted in FIG. 27(a), alternating voltage pulse of 50 V at 1 Hz is applied to drive piezoelectric element 7.

FIG. 26 shows the waveshapes of micropump states of normal condition (P), condition (Q) in which air is contained in the micropump, and condition (R) in which the micropump or needle mechanism is clogged. $V_o$ in FIG. 26 represents the standard voltage previously set in order to identify a disorder generation condition in detection circuit 708, which disorder is evaluated according to the order of showing a low (L) or a high (H) of the voltage of detection piezoelectric element 104 relative to standard voltage $V_o$ at predetermined times $T_1$, $T_2$ and $T_3$ in a period of rising voltage output pulse.

When, for example, $T_1=10$ m sec, $T_2=30$ m sec, and $T_3=50$ m sec are presumed the condition detected is as follows:

P (normal)
$(T_1, T_2, T_3) = (L, H, H)$
$= (O, I, I)$

Q (air)
$(T_1, T_2, T_3) = (H, H, H)$
$= (I, I, I)$

R (clogged)
$(T_1, T_2, T_3) = (O, O, O)$

The outlet valve has only the conditions of open or closed, so that evaluation of a normal or abnormal micropump condition is accomplished by detecting only whether the outlet valve is open or closed. In detail, the evaluation is carried out when the voltage is compared to a standard voltage after a pre-determined length of time has elapsed from the instant of rising in order to see a high and a low voltage.

FIGS. 28(a)-(e) show the relation between particular micropump disorder conditions and output waveshapes of detection piezoelectric element.

Figure 28:
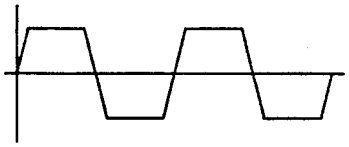
FIG. 28 depicts the relationships between micropump disorder conditions and the output waveforms at the positions the disorder is detected.
Figure 28:
Figure 28:
Figure 28:
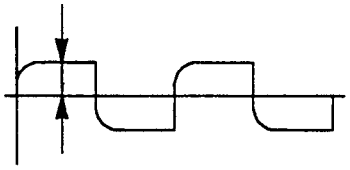
Figure 28:
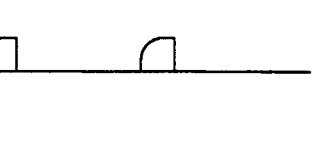
Figure 28:
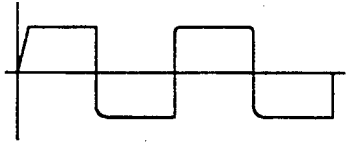
Figure 28:

FIG. 28(a) depicts waveshapes with air in the micropump. When only air is compressed, the diaphragm waveshape has a sharp rising portion and vibrates up-and-down. The outlet valve portion waveshape has little vibration.

FIG. 28(b) depicts output waveshapes when the pump mechanism, tube, and needle are clogged. The diaphragm and outlet valve portion do not substantially vibrate.

FIG. 28(c) depicts output waveshapes when the pump leaks. The resulting waveshape is the same as in FIG. 28(a).

FIG. 28(d) depicts output waveshapes when the drive piezoelectric element is cracked or a lead is broken. The amplitudes at the diaphragm and the outlet valve decrease or no output is obtained.

FIG. 28(e) depicts output waveshapes when the outlet valve is open due to back pressure or an outlet is clogged.

Resistance in the valve body is diminished and liquid flows in alternate directions at the outlet side, so the detected diaphragm waveshape has a sharp rising portion and vibrates up-and-down. The waveshape detected at the outlet valve has almost no vibration.

The negative portion of the detected waveshapes are cancelled by employing a diode so the waveshape evaluations are carried out with only the positive waveshape portions.

When a disorder occurs, deformation appears in the generated waveshape. Should the media flowing through the micropump change from a compressible to a non-compressible substance or vice versa, such change is detected in the waveshapes.

Figure 29:
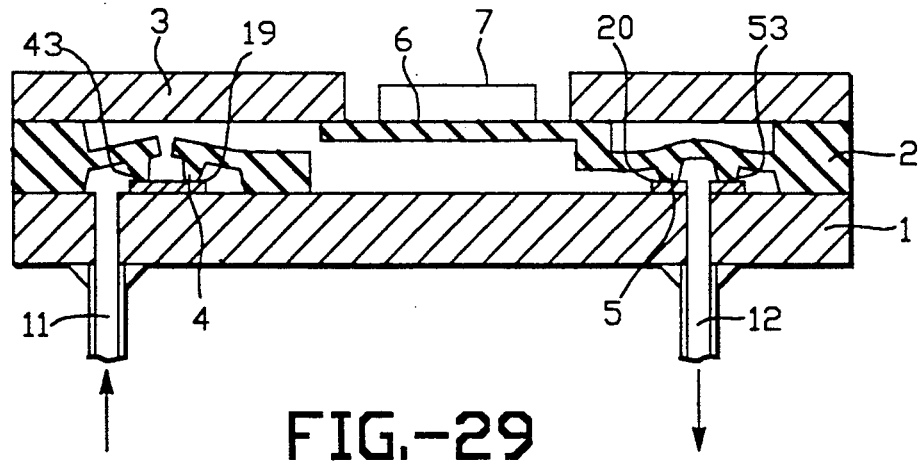
FIG. 29 depicts a method for the application of pre-pressure to the inlet and outlet port valve seal portions.

FIG. 29 illustrates structure for providing pre-pressure to seal portions 43 and 53 at the inlet and outlet valves. The micropump includes substrate 1 and a pair of adhering membranes 19 and 20 made of metal platings such as Si, Au, and Ag adhered to substrate 1. Adhering membranes on substrate 1 provides a contacting surface of uniform thickness which is easier to apply than on the valve bodies.

Figure 30A:
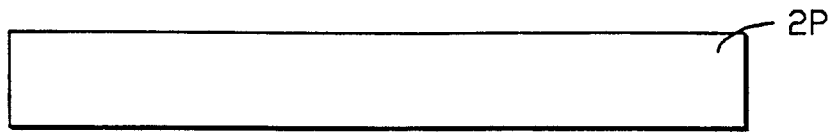
FIGS. 30(a)-(i) are sections showing the steps of manufacturing the thin membrane plate in a micropump constructed according to the present invention.
Figure 30B:
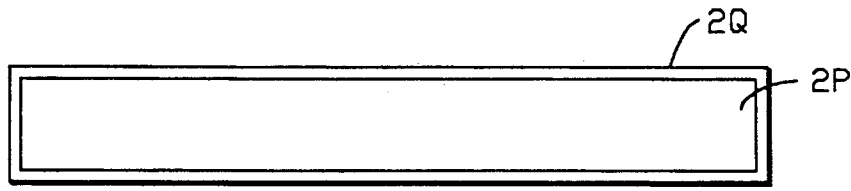
Figure 30C:
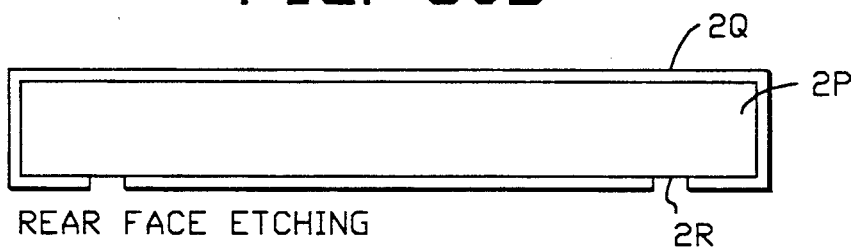

FIGS. 30(a)-(i) depict a method of manufacturing a thin membrane plate of an important member of the micropump according to the present invention. In FIG. 30(a) both faces of a silicon wafer of face-direction (100) are polished and washed to provide substrate 2P having a thickness of 280 μm. Substrate 2P is thermally oxidized in an atmosphere of $O_2$ at 1100° C. for one hour. FIG. 30(b) depicts an oxidized $SiO_2$ membrane 2Q of 0.13 μm formed on all surfaces of the substrate of FIG. 30(a). In FIG. 30(c), a resist pattern is formed at the rear face of substrate 2P on the oxidized membrane 2Q. Oxidized membrane 2Q is removed to form the pattern by means of hydrofluoric acid etching liquid. An etching mask pattern 2R is used in this first etching process to form through holes.

Figure 30D:
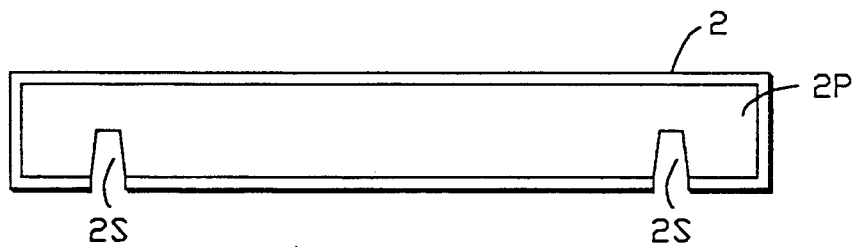

In FIG. 30(d) the first anisotropy etching to the silicon on a part of the etching mask pattern 2R is carried out in order to form non-through hole 25 of a depth of 150 μm. The etching step of substrate 2P is carried out by immersion in etching liquid. The liquid of ethylendiamine.pilocatechol.water (mol ratio is 35:5:60) is heated to 110° C. for 2 hours. To prevent the etching liquid from evaporating, a liquid returning method is employed. Non-through hole 25 having a depth of about 150 μm does not pass through substrate 2P, therefore the wafer may be handled employing vacuum chucking means. The size of other through holes may be controlled as hereinafter described.

Figure 30E:
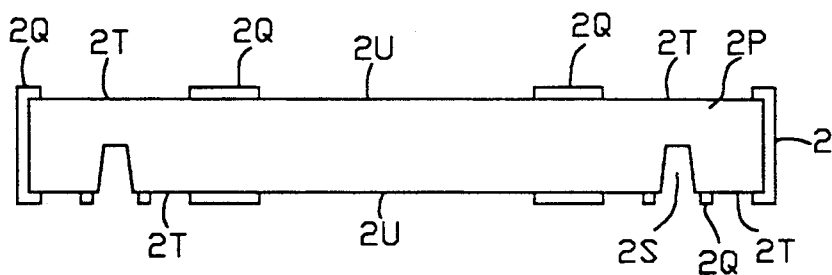

Surface patterning of oxidized membrane 2Q for producing the diaphragm, valves, and flow routes is carried out in the manner previously described to form an etching mask pattern 2T producing the valves and another etching mask pattern 2U producing the diaphragm, as shown in FIG. 30(e).

Figure 30F:
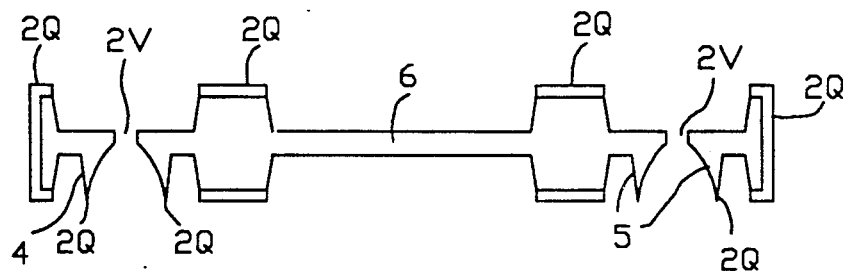
Figures 2, 30F:
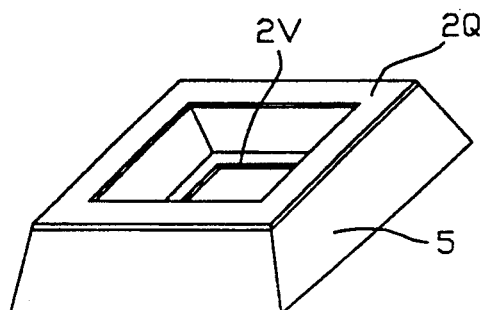

In FIG. 30(f) second anisotropy etching is performed on the silicon parts of both etching mask patterns 2T and 2U. The etching is at a depth of 110 μm on each side of substrate 2P. Diaphragm 6 having a thickness of about 60 μm and membranes of valves 4 and 5 are formed. Through holes 2V are formed at the centers of the valve membranes as shown in the enlarged view of FIG. 30 (f-2). Oxidized membrane 2Q of valves 4 and 5 surrounds the central portion of the valve membrane. Subsequently, hydrofluoric acid solution removes the oxidized membrane 2Q producing the structure illustrated in FIG. 30(g).

Figure 30G:
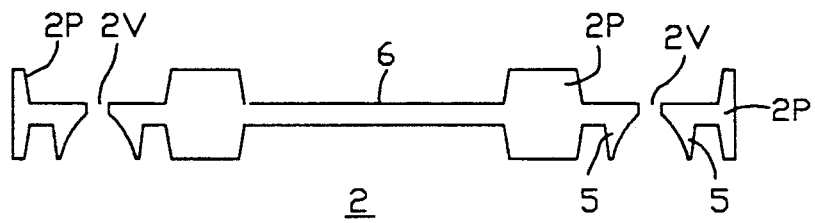
Figure 30H:
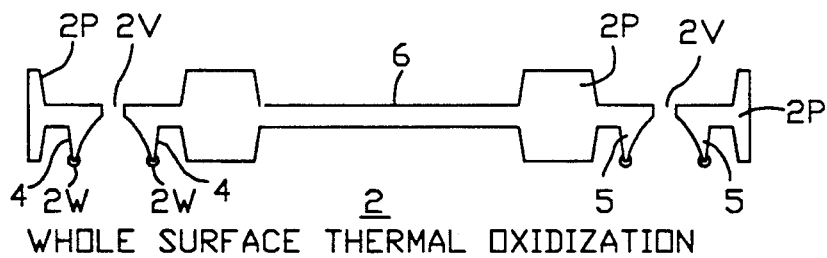

As seen in FIG. 30(h), in order to form adhering membranes 2W having a thickness of about 1 μm on the valve portions of the substrate, a mask sputtering is done on the $SiO_2$ membrane. According to the mask pattering process, a metal mask which has been formed to remove the parts of valves 4 and 5 in a separate step is applied correspondingly to substrate 2P. Then a regular high-frequency sputtering process is performed on the $SiO_2$ membrane for one hour thirty minutes to deposit $SiO_2$ of 1 μm on valves 4 and 5, resulting in formation of adhering membrane 2W. The sputtering employs Ar spatter gas pressure of $3 \times 10^{-3}$ Torr, RF power of 400 W, and a substrate temperature of 200° C.

Figure 30I:
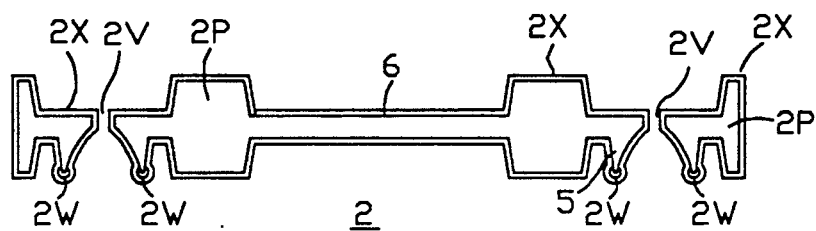
Figure 33:
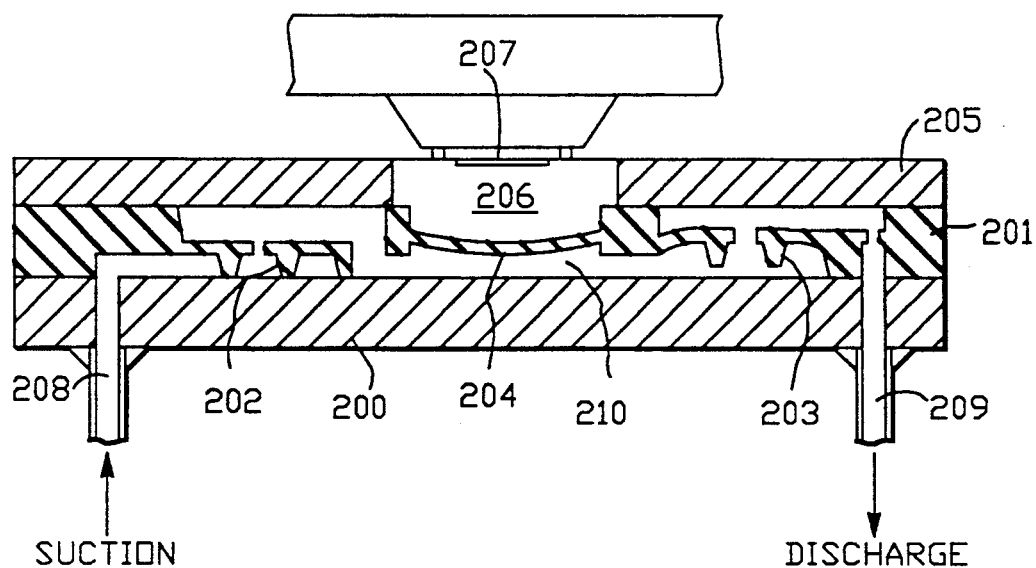
FIG. 33 is a section of a conventional micropump.

As shown in FIG. 30(i), whole surfaces of the substrate are thermally oxidized in order to form oxidized membranes 2X of thickness 0.13 μm on both surfaces. This oxidizing process is done to improve micropump anti-corrosiveness, which is necessary to provide for ease of liquid flow particularly when the transported liquid is a chemical. The oxidizing process provides the routes through which liquid flows with improved wetting power and chemical resistance. As seen in FIG. 30(i), thin membrane plate 2 is obtained by leaving about 1 μm of an oxidized adhering membrane 2W at valves 4 and 5. Adhering membrane 2W prevents adhering membrane 2 of valves 4 and 5 from coming into contact with glass in the anode joining process of subsequent micropump assembly.

The process of forming adhering membrane 2W has been explained with reference to the mask sputtering of FIGS. 30(f)-(h). However, the adhering membrane may be formed according to two alternative methods. According to a first alternative method, a $SiO_2$ membrane of 1 μm is formed on all surfaces of the substrate using a pressure-reduced CVD in an atmosphere gas of $SiH_4$ gas+$O_2$, at 400° C. and a rate of CVD of 100 A/minute for 100 minutes. A resist pattern is formed on parts for valves 4 and 5, and on the $SiO_2$ membrane except for parts removed by hydrofluoric acid etching liquid for valves 4 and 5. According to the second alternative method, ordinal wet thermal oxidation forms a $SiO_2$ membrane of 1 μm on all substrate surfaces and a $SiO_2$ membrane is left only on the parts for valves 4, 5.

The method of forming membrane plate 2, then, includes: (1) etching the substrate rear face to form non-through hole 2S and etching both faces to form through hole 2V at the center of the valve membrane and (2) forming adhering membrane 2W, for example, by a mask sputtering process on the parts of valves 4, 5 which come into contact with glass in order to prevent valves and glass from welding to each other during micropump assembly.

Figure 31:
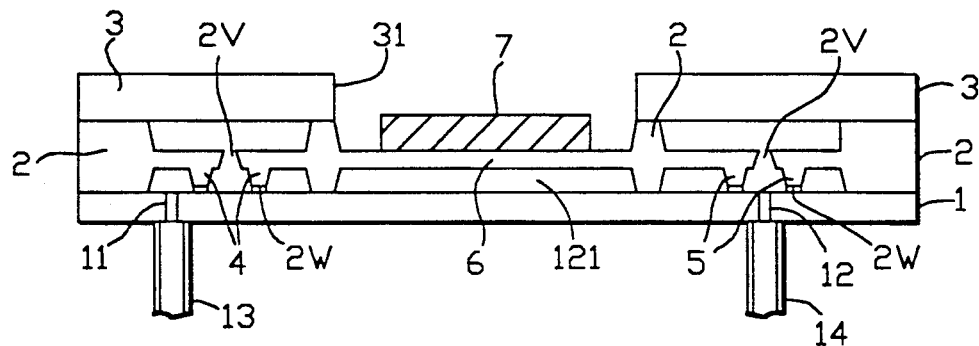
FIG. 31 is a section explaining a method how to use the thin membrane plate, constructing the micropump.
Figure 32:
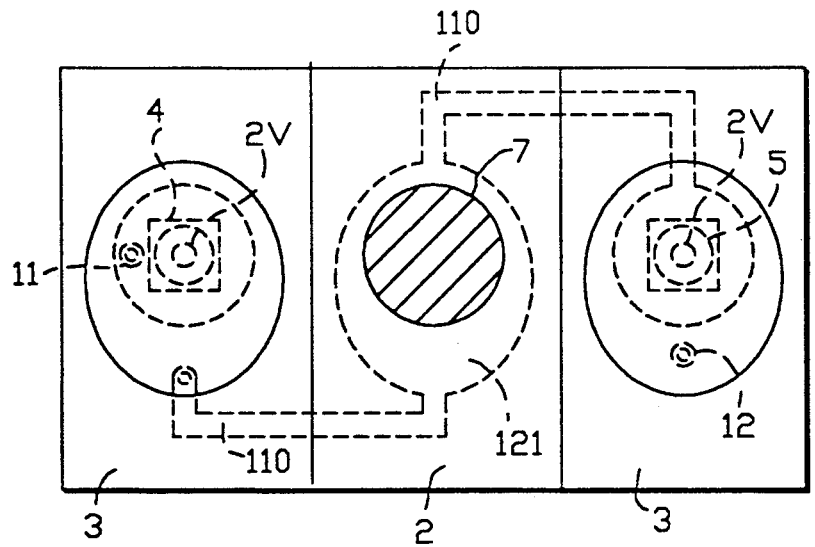
FIG. 32 is a cross-sectional view of FIG. 31.

FIGS. 31 and 32 depict a micropump assembly method employing a thin membrane plate as a pump main body. Thin membrane plate 2 is provided with diaphragm 6, valves 4, 5 having adhering membranes 2W at their ends, and flowing routes 110 correctly adhered to lower glass plate 1 at predetermined positions. Upper glass plate 3 is adhered to the top surface of membrane plate 2 to form flow routes 110 and pumping chambers 121. The upper and lower glass plates 1, 3 are made of borosilicate glass having a thickness of about 1 mm. Holes for liquid supply port 11 and liquid discharge port 12 are previously provided in lower glass plate 1 and hole 31 in which piezolelectric element 7 is installed is formed in the upper glass plate 3 at a position above diaphragm 6. Prior to the adhering step depicted in FIG. 31, the entire micropump is heated to 400° C. and anode joining is performed during which the connecting side of thin membrane plate 2 is made positive and the side of lower glass plate 1 is made negative. A DC current voltage of 1000 V is applied for 10 minutes. Further anode joining is performed after fabrication of lower glass plate 1 to which plate thin membrane plate 2 is bonded. Following two-stage anode joining, upper and lower glass plates 1 and 3, respectively, and thin membrane plate 2, except for adhering membranes 2W, are adhered.

Because oxidized membranes 2X are as thin as 0.13 μm, it is possible to join by an anode joining process. However, adhering membrane 2W is made of an oxidized membrane having a thickness of 1 μm so that an anode joining process cannot be performed, permitting the application of theabove-described micropump manufacturing method.

Following anode joining, valves 4 and 5 protrude from the bottom face of thin membrane plate 2 by the thickness of adhering membrane 2W and pre-pressure is applied to the valve membranes of valves 4 and 5. Adhering membranes 2W are compressed onto lower glass plate 1 by its thickness of 1 μm, however, valves 4 and 5 are not welded to the glass plate since glass does not anodically join to a $SiO_2$ membrane, resulting in good valve seal performance.

Supply tube 13 is joined to the bottom of supply port 11 and discharge tube 14 is joined to the bottom of discharge port 12, thus substantially completing micropump construction.

Then, the micropump manufacturing enters into a final step. The explanation of step has been done with reference to one micropump main body, however practically, a plurality of the same patterns are formed on one silicon wafer. In micropump assembly, a die cuts out pieces of the silicon wafer for one micropump, piezoelectric element (disc) 7 is adhered on the upper surface of diaphragm 6. Electric wiring (not shown) for the piezoelectric element is made, and tubings (not shown) are attached to supply port 11 and discharge port 12.

While the invention has been described in conjunction with several specific embodiments, it is evident to those skilled in the art that many further alternatives, modifications and variations will be apparent in light of the forgoing description. Thus, the invention described herein is intended to embrace all such alternatives, modifications, applications and variations as may fall within the spirit and scope of the appended claims.

What is claimed is:

1. A two-valve thin plate micropump comprising:

a pump body comprising an assembled combination of a substrate plate, an intermediate thin membrane plate, and a surface plate, said substrate plate containing therein an inlet port and an outlet port, a discharge outlet formed on a surface of said substrate axially aligned with and leading to said outlet port;

said thin membrane plate having a first major surface in surface engagement with said substrate surface;

said thin membrane plate having an integral inlet valve and an integral outlet valve for opening and closing, in a substantially fluid tight manner, access to said inlet port and outlet port, respectively;

said thin membrane plate having an integral diaphragm and an adjacent pump chamber and a fluid flow route system between said inlet and outlet ports and said pump chamber;

said surface plate in surface engagement with a second major surface of said thin membrane plate;

means for driving said diaphragm so as to open and close said valves and place them in substantially opposite open and closed states from each other;

said outlet valve having a cup-shaped valve body wherein a rim of said cup-shaped body is moved to selectively uncover and cover said discharge outlet of said outlet port in response to said diaphragm being driven, providing for a substantially uniform volume of pumped fluid through said pump within a range of pump back pressure existing at said outlet valve.

2. The micropump according to claim 1 wherein said diaphragm driving means comprises a piezoelectric element secured to said diaphragm.

3. The micropump according to claim 1 wherein said inlet port communicates with an inlet valve chamber through an intermediate chamber positioned opposite a partition above said outlet valve.

4. A micropump according to claim 3 wherein said pump chamber is in communication with an outlet valve chamber through an intermediate chamber positioned opposite a partition wall integral with said inlet valve.

5. The micropump according to claim 1 wherein a partition wall is formed in said thin membrane plate having one face thereof supporting said outlet valve and the other face thereof exposed to the exterior of said pump body.

6. The micropump according to claim 1 wherein said outlet valve is supported by a partition wall and one portion of said partition wall is openly exposed through said surface plate.

7. The micropump according to claim 1 wherein said inlet valve includes a cup shaped valve body and is positioned adjacent to an inlet of said inlet port.

8. The micropump according to claim 1 further including an intermediate substrate positioned between said substrate and said thin membrane plate, said intermediate substrate having a laterally disposed inlet port and a laterally disposed outlet port.

9. The micropump according to claim 1 wherein said thin membrane plate is divided into an upper thin membrane plate member containing an inlet valve and a pump chamber and a lower thin membrane plate member containing an outlet valve, an intermediate substrate sandwiched between said upper and lower membrane plates and providing fluid communication between said inlet valve and pump chamber of said upper membrane plate and outlet valve of said lower membrane plate, said intermediate substrate containing a first flow route leading from said inlet port to said pump chamber containing said inlet valve and a second flow route leading from said pump chamber to said outlet valve.

10. The micropump according to claim 1 wherein a support is positioned substantially at a center region of said diaphragm and extending between said diaphragm region and said substrate surface to function as a stopper to uniformly attenuate the displacement of said diaphragm upon operation of said diaphragm driving means.

11. The micropump according to claim 10 wherein said support is a cylindrically shaped projection integral with said diaphragm surface.

12. The micropump according to claim 10 wherein said support is a convex projection extending across said diaphragm surface.

13. The micropump according to claim 10 wherein a portion of said diaphragm surface is in direct contact with said substrate surface and comprising said support, transverse grooves formed across said diaphragm surface.

14. The micropump according to claim 1 wherein said diaphragm is formed as part of said surface plate, said membrane plate including a support engaging a surface of said diaphragm, said support having a flow route for communication between said pump chamber and said inlet and outlet valves, said support functioning as a stopper to uniformly attenuate the displacement of said diaphragm upon operation of said diaphragm driving means.

15. The micropump according to claim 1 wherein detection means is secured to said diaphragm for sensing operational behavior of said diaphragm driving means.

16. The micropump according to claim 15 wherein said diaphragm driving means comprises a piezoelectric element secured to said diaphragm, said detection means is a piezoelectric element secured to said piezoelectric element.

17. The micropump according to claim 1 wherein detection means is secured relative to said outlet valve for sensing operational behavior of said outlet valve.

18. The micropump according to claim 17 wherein said detection means comprises a piezoelectric element secured to an exterior surface substantially in alignment with said outlet valve, and means extending between said outlet valve to an interior surface of said surface plate opposite to said piezoelectric element to transfer the oscillatory vibrational operation of said outlet valve for detection by said piezoelectric element.

19. The micropump according to claim 17 wherein said detection means is a piezoelectric element secured to a back face of said outlet valve.

20. The micropump of claim 15 wherein the detection means includes a detection circuit for comparing the detected waveshape to a standard voltage waveshape at predetermined spatial intervals along a rising portion of said detected waveshape.

21. The micropump according to claim 1 further comprising a cup-shaped valve body provided for said inlet valve with the rim thereof in engagement with a surface of said substrate plate, membranes formed on said cup-shaped body rims of said inlet and outlet valves so that the height of said valves extend from a surface plane of said membrane plate to provide a prebiasing condition relative to the seating of said valve inlet and valve outlet on said substrate surface upon assembly of said pump body.

22. The micropump according to claim 1 wherein a thin support wall is formed in said thin membrane plate having one face thereof supporting said outlet valve, and detection means secured to the other face of said partition wall for sensing the motion of said outlet valve for determining if the micropump is functioning properly.

23. The micropump according to claim 6 wherein detection means is secured to said one portion of said partition wall for sensing the motion of said outlet valve for determining if the micropump is functioning properly.

24. The micropump according to claim 10 wherein said support comprises two or more projections extending from said diaphragm surface for engagement with said substrate surface.

25. The micropump according to claim 23 wherein said projections are concentrically positioned, cylindrically shaped projections formed on said diaphragm surface.

26. The micropump according to claim 23 wherein said projections are a plurality of projections formed in a ring on said diaphragm surface.

27. The micropump according to claim 10, wherein said support is a cylindrically shaped, hollow projection integral with said diaphragm surface.

28. A two-valve thin plate micropump comprising:

a pump body comprising an assembled combination of a substrate plate, an intermediate thin membrane plate and a surface plate, said substrate plate containing therein an inlet port and an outlet port, said thin membrane plate having a first major surface in surface engagement with said substrate surface and an integral inlet valve and an integral outlet valve for opening and closing access to said inlet port and outlet port;

said thin membrane plate having an integral diaphragm and a pump chamber formed between a first major surface of said diaphragm and a portion of said substrate surface and forming as assembled as said pump body a fluid flow route system between said inlet and outlet ports and said pump chamber;

diaphragm driving means secured to a second major surface surface of said diaphragm;

said surface plate in surface engagement with a second major surface of said thin membrane plate opposite to said first major surface;

and a support extending between said surface diaphragm and said substrate surface portion and substantially concentric relative to cross sectional length of said diaphragm to function as a stopper to uniformly attenuate the displacement of said diaphragm upon operation of said diaphragm driving means.

29. A two-valve thin plate micropump comprising:

a pump body comprising an assembled combination of a substrate plate, an intermediate thin membrane plate and a surface plate, said substrate plate containing therein an inlet port and an outlet port, said thin membrane plate having a first major surface in surface engagement with said substrate surface and an integral inlet valve and an integral outlet valve for opening and closing access to said inlet port and outlet port;

said thin membrane plate having an integral diaphragm and an adjacent pump chamber and forming as assembled as said pump body a fluid flow route system between said inlet and outlet ports and said pump chamber;

said surface plate in surface engagement with a second major surface of said thin membrane plate;

a cup-shaped valve body provided for each of said inlet and outlet valves with annular rims thereof in engagement with a surface of said substrate plate, annular membranes formed on said cup-shaped body annular valve rims so that the height of said valves extend from a surface plane of said membrane plate to provide a pre-biasing condition relative to the seating of said valve inlet and valve outlet on said substrate surface upon assembly of said pump body.

30. A two-valve thin plate micropump comprising:

a pump body comprising an assembled combination of a substrate plate, an intermediate thin membrane plate and a surface plate, said substrate plate containing therein an inlet port and an outlet port, said thin membrane plate having a first major surface in surface engagement with said substrate surface and an integral inlet valve and an integral outlet valve for opening and closing access to said inlet port and outlet port;

said thin membrane plate having an integral diaphragm and an adjacent pump chamber and forming as assembled as said pump body a fluid flow route system between said inlet and outlet ports and said pump chamber;

said surface plate in surface engagement with a second major surface of said thin membrane plate;

a thin support wall formed in said thin membrane plate having one face thereof supporting said outlet valve; and detection means secured to the other face of said partition wall for sensing the motion of said outlet valve for determining if the micropump is functioning properly.

31. The micropump of claim 30 wherein said detection means comprises a diffused resistor means formed in said partition wall.

* * * * *